(12) United States Patent
Higuchi

(10) Patent No.: US 7,570,408 B2
(45) Date of Patent: Aug. 4, 2009

(54) SURGICAL MICROSCOPE APPARATUS

(75) Inventor: Katsuhiro Higuchi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 12/216,183

(22) Filed: Jul. 1, 2008

(65) Prior Publication Data

US 2009/0015790 A1    Jan. 15, 2009

(30) Foreign Application Priority Data

Jul. 10, 2007    (JP) .............................. 2007-180829

(51) Int. Cl.
*A61B 3/10* (2006.01)
*G02B 21/00* (2006.01)

(52) U.S. Cl. .................. 359/221; 351/205; 359/381

(58) Field of Classification Search ............ 351/221, 351/220, 210, 205, 208, 206, 213; 359/629, 359/640, 368, 381, 618, 625, 636–639, 372, 359/389

See application file for complete search history.

(56) References Cited

U.S. PATENT DOCUMENTS 6,943,942 B2 * 9/2005 Horiguchi et al. ........... 359/381

7,232,222 B2 * 6/2007 Kogawa et al. .............. 351/221

FOREIGN PATENT DOCUMENTS

JP    2003-062003    3/2003

* cited by examiner

*Primary Examiner*—Scott J Sugarman
*Assistant Examiner*—Dawayne A Pinkney
(74) *Attorney, Agent, or Firm*—Edwards Angell Palmer & Dodge LLP

(57) ABSTRACT

A drive unit 5 of a surgical microscope apparatus 1 moves an entire optical system horizontally. A driver 175 moves a head lens 13 vertically. An imaging device 56*a* detects reflected light (observation light) of illumination light guided by an observation optical system 30. A controller 60 obtains a cross-sectional shape of the observation light based on the result of the detection of the observation light by the imaging device 56*a*, and controls the drive unit 5 to move the optical system horizontally so that this cross-sectional shape becomes a specified reference cross-sectional shape. Moreover, the controller 60 obtains the luminance distribution of the observation light based on the result of the detection of the observation light by the imaging device 56*a*, and controls the driver 175 to move the head lens 13 vertically so that this luminance distribution becomes a specified reference distribution profile.

17 Claims, 13 Drawing Sheets

SURGICAL MICROSCOPE APPARATUS

BACKGROUND OF THE INVENTION

1. Field of the Invention

The present invention relates to a surgical microscope apparatus used in an opthalmological surgery, and particularly relates to a surgical microscope apparatus comprising a head lens that focuses illumination light to illuminate the interior of an eye.

2. Description of the Related Art

In a conventional vitreoretinal surgery in the opthalmology field, the interior of an eye is observed by placing a surgical contact lens on the cornea and inserting a light guide (an optical fiber) into the interior of the eye to illuminate a surgical site. In this method, an operator holds the light guide in one hand and a surgical instrument in the other hand. Therefore, there has been such a problem that it is hard to perform a precise operation.

To solve this problem, a surgical microscope apparatus comprising a lens (a head lens) between an eye and an objective lens has been proposed (refer to Japanese unexamined patent application publication JP-A 2003-62003, for example). The head lens acts so as to focus illumination light passed through the objective lens and guide it to the interior of the eye. In practical use, a plurality of head lenses having different refractive powers are provided. These head lenses are selectively used depending on positions to observe the fundus oculi, etc.

An example of a surgical microscope apparatus having a head lens is shown in FIG. 15 and FIG. 16. A surgical microscope apparatus 100 is used to observe an eye E in a surgery of the fundus oculi (retina) Er, cornea Ec, crystalline lens El, etc.

One end of a first arm 3 is connected to the upper end of a supporting post 2 of the surgical microscope apparatus 100. One end of a second arm 4 is connected to the other end of the first arm 3. A drive unit 5 is connected to the other end of the second arm 4. An operator's microscope 6 is suspended from the drive unit 5. An assistant's microscope 7 is disposed together with the operator's microscope 6.

The surgical microscope apparatus 100 is provided with a foot switch 8. The operator operates the surgical microscope apparatus 100 by operating the foot switch 8 with his/her foot. The drive unit 5 vertically and horizontally moves the operator's microscope 6 and the assistant's microscope 7 in response to the operation by the foot switch 8, etc.

Various types of optical systems and drive systems are housed in a lens barrel part 10 of the operator's microscope 6. An inverter part 12 is disposed at the upper part of the lens barrel part 10. The inverter part 12 is an optical unit that converts an observation image obtained as a reverted image into an erected image. Right and left eye pieces 11L and 11R are disposed at the upper part of the inverter part 12.

Moreover, the upper edge of a holding arm 14 is connected to the operator's microscope 6. A head lens 13 is held at the lower edge of the holding arm 14. The upper edge of the holding arm 14 is pivotally disposed so that the holding arm 14 is rotatable in the vertical direction. Consequently, it is possible to insert the head lens 13 into a position between the eye E and an objective lens 15, and retract it from the position. The head lens 13 and the holding arm 14 are housed in a housing part, which is not shown in the drawings.

An optical system shown in FIG. 16 is housed in the lens barrel part 10 of the operator's microscope 6. FIG. 16 is a side view of the optical system seen from the side of the assistant's microscope 7. This optical system includes an illumination optical system 20 and observation optical systems 30.

The observation optical systems 30 are disposed on the respective sides of an optical axis O of the objective lens 15. Each of the observation optical systems 30 includes a zoom lens system 31, a beam splitter 32, an imaging lens 33, an image-erecting prism 34, an interpupillary adjusting prism 35, a field diaphragm 36, and an eyepiece 37.

The zoom lens system 31 is composed of a plurality of zoom lenses 31a, 31b and 31c. The beam splitter 32 separates part of light coming from the eye E, and guides it to the assistant's microscope 7 or a TV camera (not shown).

The illumination optical system 20 includes an illumination light source 21, a condenser lens 22, an illumination field diaphragm 23, a slit plate 24, an illumination prism 25, and a collimator lens 27.

A slit hole 24a is formed on the slit plate 24. Moreover, the slit plate 24 can be inserted into and retracted from an illumination light path of the illumination optical system 20. When being inserted in the illumination light path, the slit plate 24 can be moved in a direction orthogonal to an illumination optical axis O'. The slit hole 24a is formed in a direction orthogonal to both the illumination light axis O' and a movable direction of the slit plate 24. A projection image of the slit hole 24a to a fundus oculi Er is formed in parallel to a plane including observation light axes of the right and left observation optical systems 30.

The illumination field diaphragm 23 is disposed at a position optically conjugate to an anterior focus position F of the objective lens 15. The slit plate 24 is placed near the illumination field diaphragm 23. The slit hole 24a is formed at a position substantially optically conjugate to the anterior focus position F. The position of the objective lens 15 is adjusted so that the anterior focus position F becomes conjugate to a fundus oculi Er (retina).

The illumination light source 21 may be housed in the lens barrel part 10, or may be disposed outside the lens barrel part 10. In the latter case, illumination light outputted from the illumination light source 21 is guided through an optical fiber to the condenser lens 22 within the lens barrel part 10.

When illumination light is projected to the eye E, the cornea Ec acts as a convex reflection mirror, and part of the illumination light is reflected. When this corneal reflection light enters the observation field (namely, mixes into the fundus oculi reflection light), flare occurs within the observation field and prevents observation.

In the conventional surgical microscope apparatus, the distance between the head lens 13 and the cornea Ec is adjusted manually, thereby preventing corneal reflection light from mixing into fundus oculi reflection light.

Moreover, when the position of the eye E changes, it is necessary to adjust the positions of the optical systems 20, 30 and the head lens 13 in order to observe a target site. This position adjustment is also manually performed by the operator conventionally.

Thus, according to the conventional surgical microscope apparatus, the positional relationship between an eye and a device optical system is manually adjusted, so that there are problems that the concentration of the operator is disturbed, the operation is complicated, and the surgical time is long. Moreover, it is not easy for a not-expert person to manually adjust the positions.

SUMMARY OF THE INVENTION

The present invention has been made to solve such problems and an object of the present invention is to provide a surgical microscope apparatus that makes it possible to easily adjust the positional relationship between an eye and an optical system.

In order to achieve the abovementioned object, in a first aspect of the present invention, a surgical microscope apparatus comprises: an optical system including an illumination optical system configured to project illumination light onto an eye via an objective lens, an observation optical system configured to guide reflected light of the illumination light from the eye to an eyepiece via the objective lens, and a head lens positioned between the objective lens and the eye; a driver configured to move the optical system; a detector configured to detect the reflected light guided by the observation optical system; and a controller configured to control the driver to change a relative position of the optical system with respect to the eye so that a cross-sectional pattern of the reflected light detected by the detector becomes a specified reference pattern.

Further, in a second aspect of the present invention, the surgical microscope apparatus of the first aspect is characterized in that: the illumination optical system projects light having a cross-section with a specified shape as the illumination light; and the controller includes an analyzer configured to obtain a cross-sectional pattern of the reflected light based on a result of detection of the reflected light by the detector.

Further, in a third aspect of the present invention, the surgical microscope apparatus of the second aspect is characterized in that the analyzer obtains luminance distribution in a cross-section of the reflected light as the cross-sectional pattern.

Further, in a fourth aspect of the present invention, the surgical microscope apparatus of the third aspect is characterized in that: the specified reference pattern is a reference distribution profile of luminance corresponding to the specified shape of the illumination light; the driver includes a first drive mechanism configured to move the head lens in a direction of an optical axis of the objective lens; and the controller controls the first drive mechanism so that a profile of luminance distribution of the reflected light becomes the reference distribution profile.

Further, in a fifth aspect of the present invention, the surgical microscope apparatus of the fourth aspect of the present invention is characterized in that the controller includes a storage configured to previously store an allowable range of luminance distribution based on the reference distribution profile and a determining part configured to determine whether the luminance distribution of the reflected light is within the allowable range, and controls the first drive mechanism so that it is determined that the luminance distribution is within the allowable range.

Further, in a sixth aspect of the present invention, the surgical microscope apparatus of the fourth aspect of the present invention is characterized in that: the specified shape of a cross-section of the illumination light is rectangular; and the reference distribution profile is a rectangular pulse shape.

Further, in a seventh aspect of the present invention, the surgical microscope apparatus of the fifth aspect of the present invention is characterized in that: the specified shape of the cross-section of the illumination light is rectangular; and the reference distribution profile is a rectangular pulse shape.

Further, in an eighth aspect of the present invention, the surgical microscope apparatus of the third aspect of the present invention is characterized in that: the driver includes a first drive mechanism configured to move the head lens in a direction of an optical axis of the objective lens; and the controller includes a computing part configured to obtain a movement direction and/or movement amount of the head lens based on the luminance distribution of the reflected light, and controls the first drive mechanism based on the movement direction and/or the movement amount.

Further, in a ninth aspect of the present invention, the surgical microscope apparatus of the eighth aspect of the present invention is characterized in that: the controller controls the first drive mechanism to move the head lens after the luminance distribution of the reflected light is acquired by the analyzer; the detector detects the reflected light of the illumination light after movement of the head lens; the analyzer obtains new luminance distribution based on the result of detection of the reflected light; and the computing part compares the luminance distribution before the movement with the new luminance distribution, and obtains the movement direction and/or movement amount of the head lens.

Further, in a tenth aspect of the present invention, the surgical microscope apparatus of the second aspect of the present invention is characterized in that the analyzer obtains a cross-sectional shape of the reflected light as the cross-sectional pattern.

Further, in an eleventh aspect of the present invention, the surgical microscope apparatus of the tenth aspect of the present invention is characterized in that: the specified reference pattern is a reference cross-sectional shape corresponding to the specified shape of the illumination light; the driver includes a second drive mechanism configured to move the optical system in a direction orthogonal to an optical axis of the objective lens; and the controller controls the second drive mechanism so that the cross-sectional shape of the reflected light becomes the reference cross-sectional shape.

Further, in a twelfth aspect of the present invention, the surgical microscope apparatus of the eleventh aspect of the present invention is characterized in that the controller includes a storage configured to previously store an allowable range of the cross-sectional shape based on the reference cross-sectional shape and a determining part configured to determine whether the cross-sectional shape of the reflected light is within the allowable range, and controls the second drive mechanism so that it is determined that the cross-sectional shape is within the allowable range.

Further, in a thirteenth aspect of the present invention, the surgical microscope apparatus of the eleventh aspect of the present invention is characterized in that: the specified shape of the cross-section of the illumination light is rectangular; and the reference cross-sectional shape is rectangular.

Further, in a fourteenth aspect of the present invention, the surgical microscope apparatus of the twelfth aspect of the present invention is characterized in that: the specified shape of the cross-section of the illumination light is rectangular; and the reference cross-sectional shape is rectangular.

Further, in a fifteenth aspect of the present invention, the surgical microscope apparatus of the eleventh aspect of the present invention is characterized in that: the driver includes a second drive mechanism configured to move the optical system in a direction orthogonal to an optical axis of the objective lens; and the controller includes a computing part configured to obtain a movement direction and/or movement amount of the optical system based on the cross-sectional shape of the reflected light and the reference cross-sectional shape, and controls the second drive mechanism based on the movement direction and/or the movement amount.

Further, in a sixteenth aspect of the present invention, the surgical microscope apparatus of the fifteenth aspect of the present invention is characterized in that: the specified shape of the cross-section of the illumination light is rectangular; the reference cross-sectional shape is rectangular; and the computing part obtains a barycentric position of the cross-sectional shape of the reflected light, obtains a distance from the barycentric position to each of four sides of the cross-sectional shape and, for two pairs of two facing sides in the cross-sectional shape of the reflected light, obtains the movement direction and/or movement amount of the optical system such that the distances to the two sides of each of the pairs are equal.

Further, in a seventeenth aspect of the present invention, the surgical microscope apparatus of the fifteenth aspect of the present invention is characterized in that: the controller controls the second drive mechanism to move the optical system after the cross-sectional shape of the reflected light is acquired by the analyzer; the detector detects the reflected light of the illumination light after movement of the optical system; the analyzer obtains a new cross-sectional shape based on a result of detection of the reflected light; and the computing part compares the cross-sectional shape before the movement with the new cross-sectional shape, and obtains the movement direction and/or movement amount of the optical system.

According to the surgical microscope apparatus according to the present invention, it is possible to project illumination light to the eye, detect the reflected light of the illumination light by the eye, and change a relative position of the optical system with respect to the eye so that the cross-sectional pattern of this reflection light becomes a specified reference pattern. Therefore, it is possible to easily adjust the positional relationship between the eye and the optical system, when compared with a conventional manual operation.

DETAILED DESCRIPTION OF THE PREFERRED EMBODIMENTS

An embodiment of a surgical microscope apparatus according to the present invention will be described in detail with reference to the drawings.

The surgical microscope apparatus according to the present invention functions to detect reflected light of illumination light projected onto an eye and adjust the position of an optical system by using a cross-sectional pattern of the reflected light as an index of a relative position of the optical system with respect to the eye. Consequently, the problems in conventional opthalmological surgery, such as the concentration of an operator is disturbed, the operation is complicated, and the surgery takes long, will be solved.

Here, the "cross-sectional pattern of the reflected light" is information showing the morphology of the cross-section of the reflected light, which is morphology information described later. The cross-sectional pattern includes, for example, information showing the light intensity of the reflected light at various positions on the cross-section, and information showing the shape of the cross-section of the reflected light. The cross-section of the reflected light is a cross-section made by a plane (substantially) orthogonal to the traveling direction of the reflected light.

Figure 15:
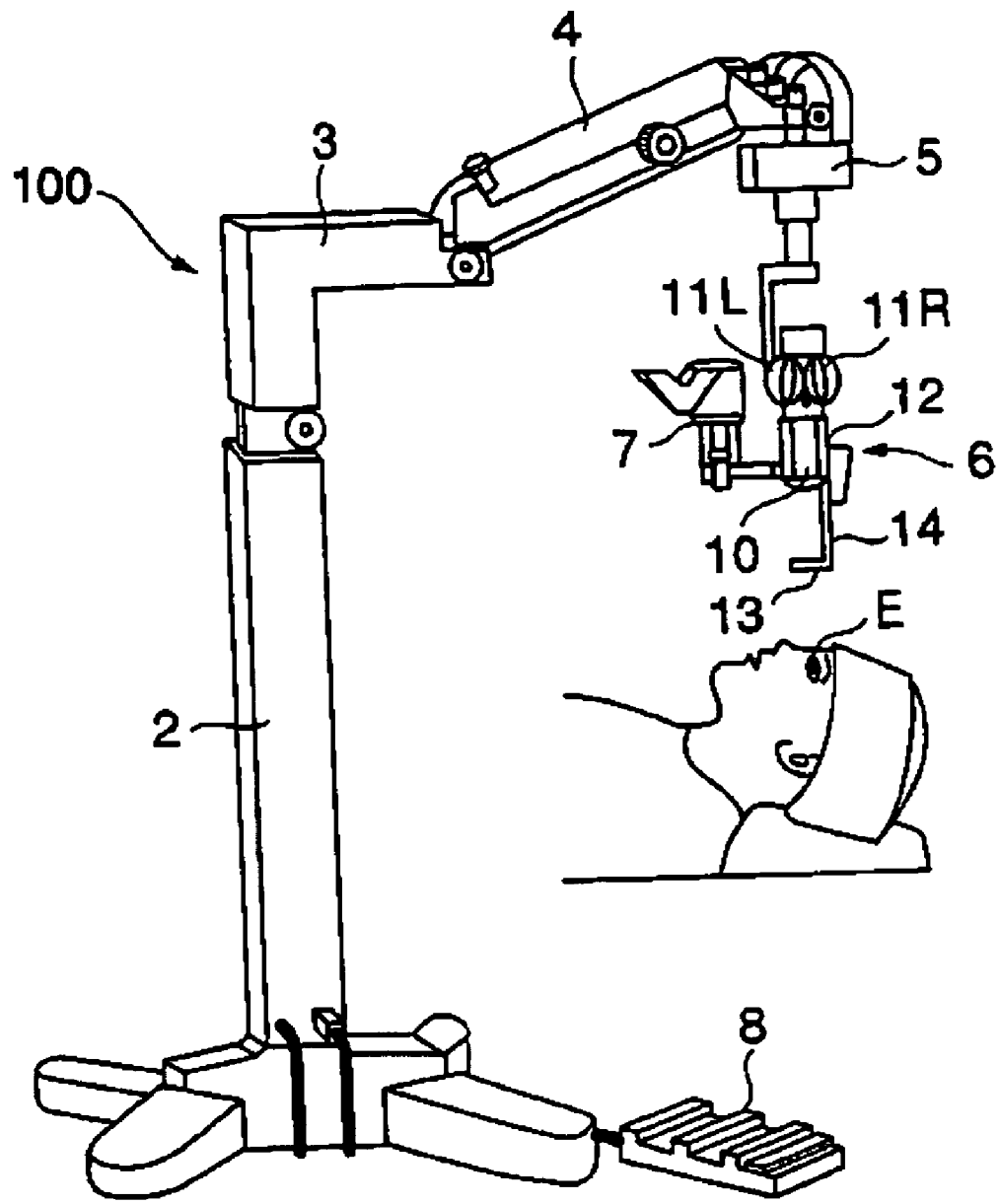
FIG. 15 is a schematic view illustrating an example of the appearance of a surgical microscope apparatus.
Figure 16:
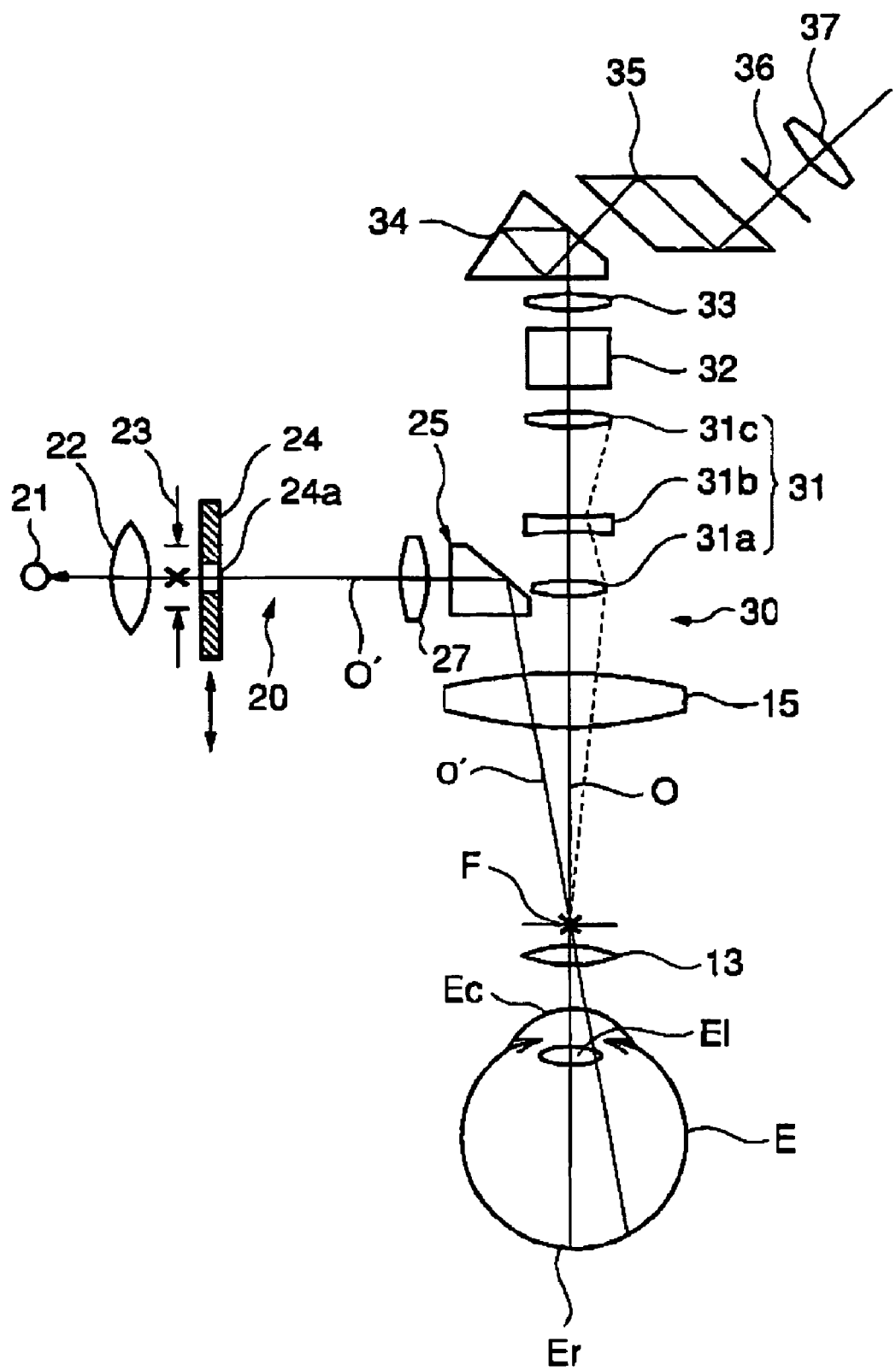
FIG. 16 is schematic view illustrating an example of the configuration of an optical system of the surgical microscope apparatus.

Below, the components similar to those of the conventional surgical microscope apparatus will be described with the same reference numerals as in FIG. 15 and FIG. 16.

First Embodiment

[Appearance]

Firstly, the appearance of a surgical microscope apparatus according to a first embodiment of the present invention will be described.

The surgical microscope apparatus according to the present embodiment, similarly to the conventional surgical microscope apparatus (refer to FIG. 15), comprises a supporting post 2, a first arm 3, a second arm 4, a drive unit 5, an operator's microscope 6, an assistant's microscope 7, and a foot switch 8.

The drive unit 5 3-dimensionally moves the operator's microscope 6 and the assistant's microscope 7. The drive unit 5 includes an actuator such as a motor. The drive mechanism 5 is an example of the "second drive mechanism" of the present invention.

Figure 1:
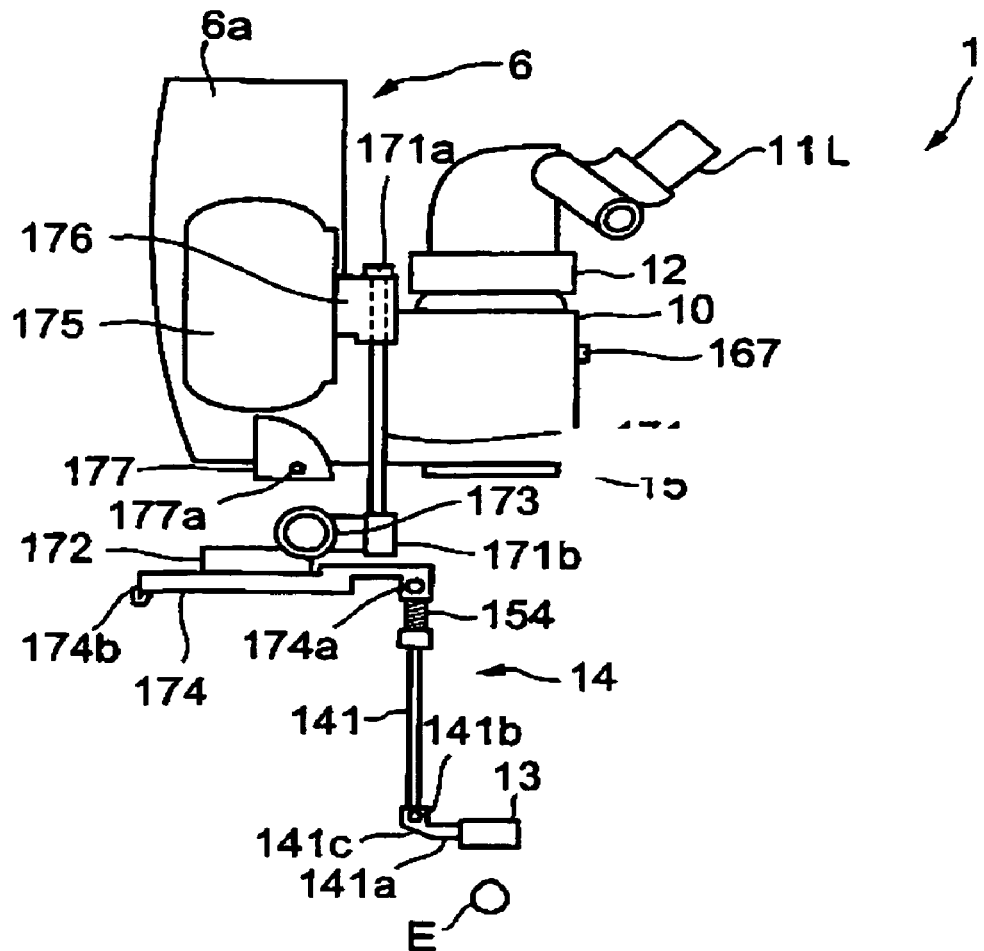
FIG. 1 is a schematic view illustrating an example of the appearance of an embodiment of a surgical microscope apparatus according to the present invention.

The appearance of the operator's microscope 6 is shown in FIG. 1. Various kinds of optical systems, a drive system, etc., are housed in a lens barrel part 10 of the operator's microscope 6. An inverter part 12 is provided above the lens barrel part 10. The inverter part 12 converts an observation image obtained as a reverted image into an erected image. A pair of eyepieces 11L and 11R on the left and right are provided above the inverter part 12.

Moreover, a head lens 13 is connected to the operator's microscope 6 via a holding arm 14. The head lens 13 is configured so as to be insertable into and retractable from a position on the optical axis of an objective lens 15. In particular, during observation of an eye E, the head lens 13 can be positioned at a position between an anterior focus position of the objective lens 15 and the eye E (referred to as a "usage position"). The head lens 13 focuses illumination light to illuminate the interior of the eye E. The objective lens 15 is provided at the bottom of the lens barrel part 10.

As the head lens 13, a plurality of lenses having different refractive powers (for example, 40 D, 80 D, 120 D, etc.) are provided, and are selectively used.

The head lens 13 is held by a holding plate 141a formed so as to encompass it. The holding plate 141a is connected to an arm part 141 via an axis 141b, and is rotatable around the axis 141b. A slope 141c is formed on the holding plate 141a.

A coil spring 154 is wound around the upper end of the arm part 141. The upper end of the arm part 141 is pivotally disposed to one end of a housing part 174 by an axis 174a. The arm part 141 is provided with a head-lens operating knob (not shown) extending horizontally when viewed from the operator side. By grasping this head-lens operating knob and swiveling the holding arm 14 around the axis 174a, the operator can position the head lens 13 to the abovementioned usage position as well as to a housing position described later.

A main body 6a of the operator's microscope 6 has a driver 175. The driver 175 is an example of the "first drive mechanism" of the present invention. To the driver 175, an up-and-down arm 171 is connected via a supporting member 176. At the upper end of the up-and-down arm 171, a fringe part 171a is formed to prevent the up-and-down arm 171 from falling from the supporting member 176. The driver 175 moves the up-and-down arm 171 vertically, together with the supporting member 176. When the up-and-down arm 171 is moved, the head lens 13 is also moved integrally.

A connecting part 171b is connected to the lower end of the up-and-down arm 171. An elevation restraining member 172 is connected to the connecting part 171b. The elevation restraining member 172 contacts an elevation restraining member 177 on the side of the main body 6a when the up-and-down arm 171 is elevated to a specified position. Thus, the elevation restraining members 172 and 177 act to prevent the up-and-down arm 171 from moving more upwardly than the specified position.

A coupling knob 173 is disposed to the connecting part 171b. The coupling knob 173 has a rotating screw (not shown). When the coupling knob 173 is rotated in a specified direction, the tip of the rotating screw is fitted into a coupling hole 177a. Consequently, the head lens 13, the holding arm 14, the housing part 174, etc., are coupled to the main body 6a. In this coupling state, movement of the head lens 13, etc. is inhibited.

Figure 2:
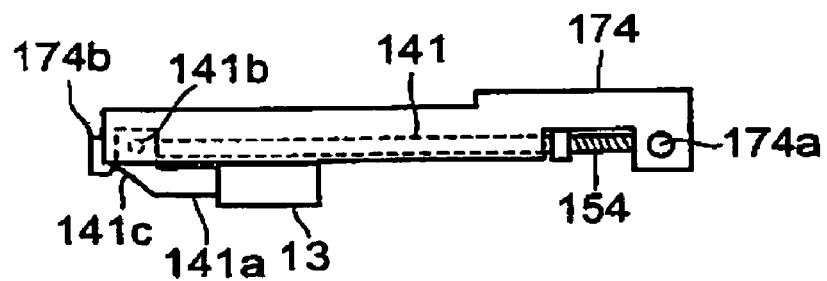
FIG. 2 is schematic view illustrating an example of the appearance of the embodiment of the surgical microscope apparatus according to the present invention.

The housing part 174 is connected to the elevation restraining member 172. The housing part 174 houses the holding arm 14 (and the head lens 13). FIG. 2 shows a state in which the holding arm 14 is housed. On the lower face of the housing part 174, a concave housing part is formed along the longitudinal direction of the housing part 174. The holding arm 14 is by swiveled around the axis 174a to be housed into the housing part.

In the state in which the holding arm 14 is housed, as shown in FIG. 2, the lens faces of the head lens 13 are directed in the vertical direction. This is because of the action of the slope 141c of the holding plate 141a and a contacting member 174b attached to the end of the housing part 174. That is, when the arm part 141 is swiveled upward around the axis 174a, the slope 141c comes in contact with the contacting member 174b and, guided along the slope 141c, the holding plate 141a rotates around the axis 141b. Consequently, the head lens 13 is positioned in the housing position in a state as shown in FIG. 2.

FIG. 1 shows a state where the head lens 13 is inserted in the usage position between the eye E and the objective lens 15. To house the head lens 13 from this state, the operator grasps the abovementioned head-lens operating knob and swivels the holding arm 14 upward, thereby housing the head lens 13 and the holding arm 14 into the housing part 174. On the other hand, to bring the head lens 13 housed in the housing part 174 into the usage state, the holding arm 14 is swiveled downward in a reverse manner.

The housing part 174 is formed so as to be attachable to and detachable from the elevation restraining member 172. This is for removing the head lens 13 and the holding arm 14 from the operator's microscope 6 when sterilizing them. A part including the housing part 174 and the head lens 13 is integrally composed. In a state in which the head lens 13, etc., are removed, the surgical microscope apparatus 1 can be used as a surgical microscope apparatus without the head lens 13.

[Configuration of the Optical System]

Figure 3:
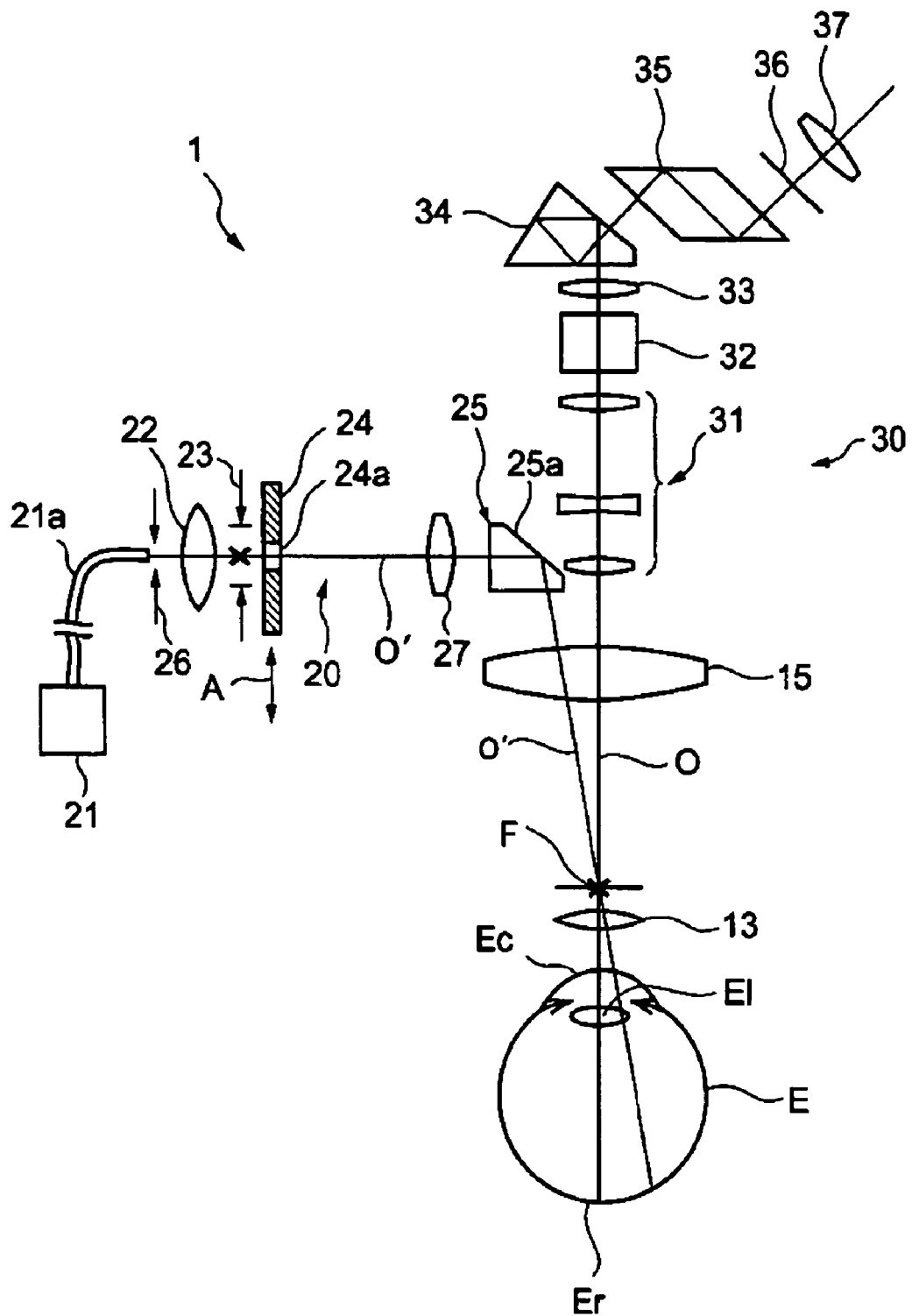
FIG. 3 is a schematic view illustrating an example of the configuration of an optical system of the embodiment of the surgical microscope apparatus according to the present invention
Figure 4:
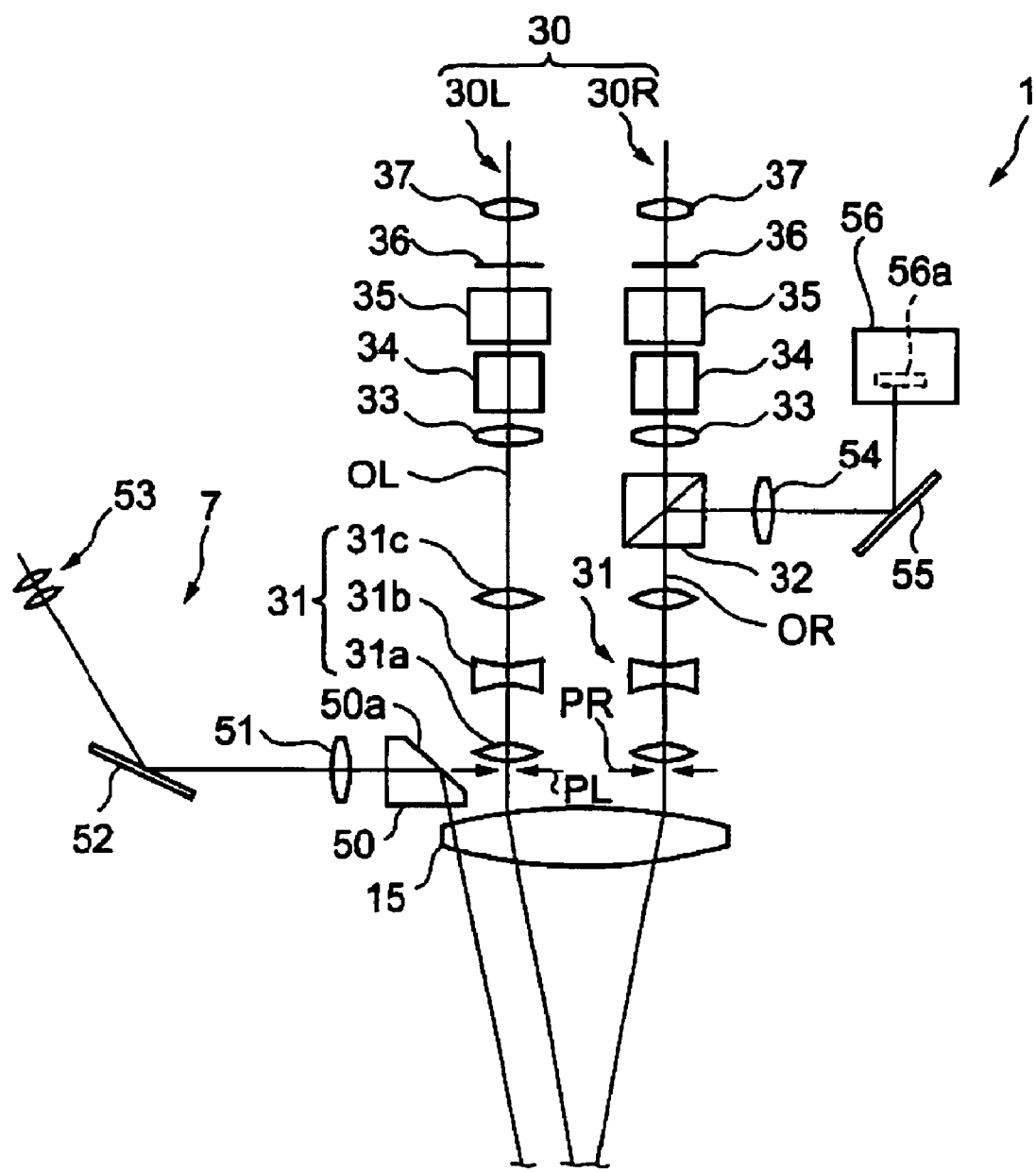
FIG. 4 is a schematic view illustrating an example of the configuration of the optical system of the embodiment of the surgical microscope apparatus according to the present invention.

FIG. 3 and FIG. 4 show the configuration of the optical system of the surgical microscope apparatus 1. Here, FIG. 3 is a view taken from the side of the assistant's microscope 7, and FIG. 4 is a view taken from the operator side. In this embodiment, the vertical direction, the horizontal direction, the anteroposterior direction, etc., are directions taken from the operator side unless stated otherwise.

[Observation Optical System]

A pair of observation optical systems 30 are provided as shown in FIG. 4. The observation optical system 30L on the left side is referred to as a left observation optical system. The observation optical system 30R on the right side is referred to as a right observation optical system. Symbol OL indicates the observation optical axis of the left observation optical system 30L. The symbol OR indicates the observation optical axis of the right observation optical system 30R. The right and left observation optical systems 30L and 30R are formed to sandwich the optical axis O of the objective lens 15.

Each of the right and left observation optical systems 30R and 30L has a zoom lens system 31, a beam splitter 32 (disposed to only the right observation optical system 30R), an imaging lens 33, an image-erecting prism 34, an interpupillary-adjusting prism 35, a field diaphragm 36, and an eyepiece 37. The zoom lens system 31 includes a plurality of zoom lenses 31a, 31b and 31c.

The beam splitter 32 of the right observation optical system 30R separates part of observation light guided along an observation optical axis OR from the eye E, and guides it to a TV-camera imaging system. This TV-camera imaging system includes an imaging lens 54, a reflecting mirror 55, and a TV camera 56.

The TV camera 56 has an imaging device 56a. The imaging device 56a is composed of, for example, a CCD (Charge Coupled Devices) image sensor, and a CMOS (Complementary Metal Oxide Semiconductor) image sensor. As the imaging device 56a, a device with a 2-dimensional receiving face is used, for example.

When the surgical microscope 1 is in use, a reception face of the imaging device 56a is positioned, for example, at a position optically conjugate to the surface of a cornea Ec, or a position optically conjugate to the position distant only ½ of the corneal curvature radius from the corneal apex in the depth direction.

The assistant's microscope 7 is a microscope used by an assistant who assists the operator. The assistant's microscope 7 is provided with an optical system forming right and left observation light paths via the objective lens 15. This optical system includes a prism 50, an imaging lens 51, a reflecting mirror 52, and an eyepiece 53, as shown in FIG. 4.

The prism 50 is provided near the circumferential end of the objective lens 15. Observation light from the eye E enters the prism 50 via the objective lens 15, and is reflected by a reflecting face 50a. The observation light is then focused by the imaging lens 51, reflected by the reflecting mirror 52, and guided to the eyepiece 53. An entrance pupil of the optical system of the assistant's microscope 7 is the reflecting face 50a of the prism 50.

A dedicated zoom lens system may be disposed to the assistant's microscope 7, though illustration thereof is omitted. In that case, it is desirable to interlock a zoom magnification of the assistant side with a zoom magnification of the operator side (a zoom magnification by the zoom lens system 31).

[Illumination Optical System]

An illumination optical system 20 comprises an illumination light source 21, an optical fiber 21a, an emission diaphragm 26, a condenser lens 22, an illumination field diaphragm 23, a slit plate 24, a collimator lens 27, and an illumination prism 25 as shown in FIG. 3.

The illumination field diaphragm 23 is provided at a position optically conjugate with an anterior focus position F of the objective lens 15.

Moreover, a slit hole 24a of the slit plate 24 is formed at a position optically substantially conjugate with the anterior focus position F.

In addition, at the time of observation of the eye E, the vertical position of the lens barrel part 10 is adjusted so that the anterior focus position F of the objective lens 15 is conjugate with a fundus oculi Er.

The illumination light source 21 is provided outside the lens barrel part 10 of the operator's microscope 6. One end of the optical fiber 21a is connected to the illumination light source 21. The other end of the optical fiber 21a is positioned at a position facing the condenser lens 22 in the lens barrel part 10. Illumination light outputted from the illumination light source 21 is guided by the optical fiber 21a, and enters the condenser lens 22.

The emission diaphragm 26 is provided at a position facing the emission opening of the optical fiber 21a (a fiber end on the side of the condenser lens 22). The emission diaphragm 26 acts so as to shield a partial region of the emission opening of the optical fiber 21a. When the region shielded by the emission diaphragm 26 is changed, the emission region of the illumination light is changed. Consequently, it is possible to change the projection angle by the illumination light, i.e., the angle formed by the incident direction of the illumination light into the eye E, and the optical axis O of the objective lens 15, etc.

Figure 5:
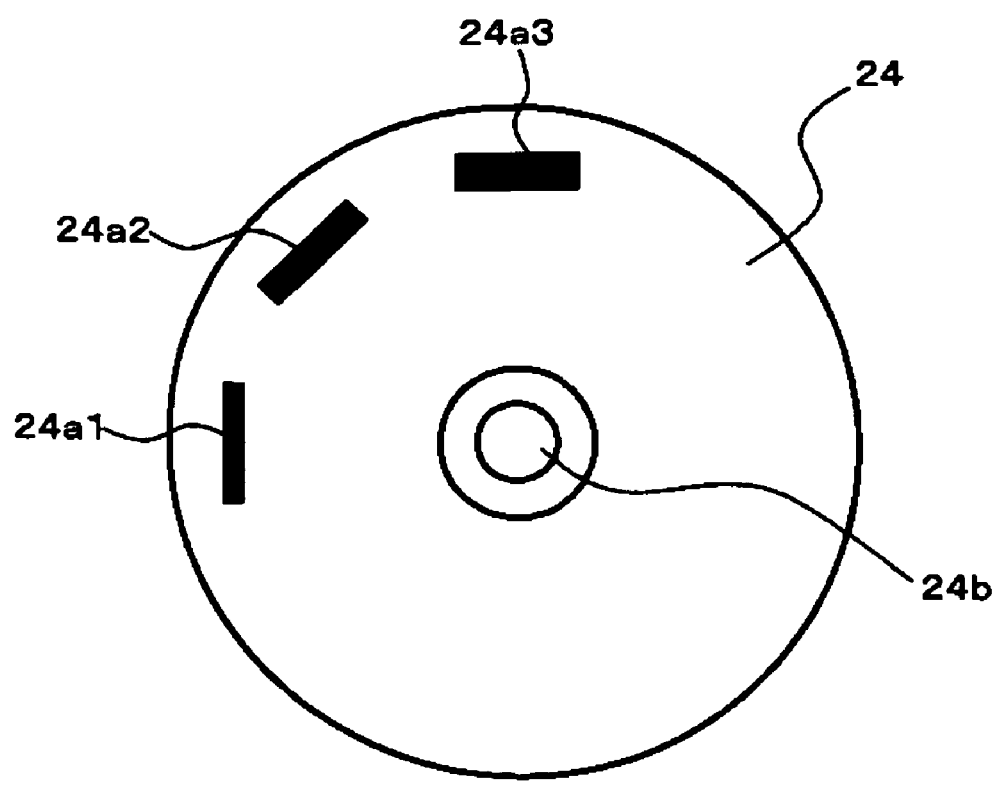
FIG. 5 is a schematic view illustrating an example of the configuration of the optical system of an embodiment of the surgical microscope apparatus according to the present invention.

The slit plate 24, for example, as shown in FIG. 5, has a plurality of rectangular slit holes 24a1, 24a2 and 24a3. The slit plate 24 is formed, for example, by a disk-shaped member with a light blocking characteristic. Thus, the slit plate 24 generates illumination light having a rectangular cross-section.

The slit holes 24a1, 24a2 and 24a3 have different slit widths from each other. For example, the slit widths of the slit holes 24a1, 24a2 and 24a3 are set to 2.5 mm, 5 mm and 9 mm, respectively. The number of the slit holes and the slit widths thereof are not limited to the above case.

Moreover, the slit plate 24 has a rotation axis 24b at the central position. The rotation axis 24b is connected to a drive mechanism (described later) rotationally drives the slit plate 24. The slit holes 24a1, 24a2 and 24a3 are formed at positions equally distant from the rotational center of the slit plate 24, respectively. Consequently, it is possible, by rotating the slit plate 24, to selectively position the slit holes 24a1, 24a2 and 24a3 on an illumination light path of the illumination optical system 20. At this moment, the slit holes 24a1, 24a2 and 24a3 positioned on the illumination light path function as the slit hole 24a in FIG. 3.

Moreover, the slit plate 24 is moved in a direction orthogonal to an illumination optical axis O' by the drive mechanism.

The collimator lens 27 makes the illumination light having passed through the slit hole 24a into a parallel light flux. The illumination light having become the parallel light flux is reflected on the reflecting face 25a of the illumination prism 25 to enter the objective lens 15, and is further passed through the head lens 13 to enter the eye E.

Figure 6:
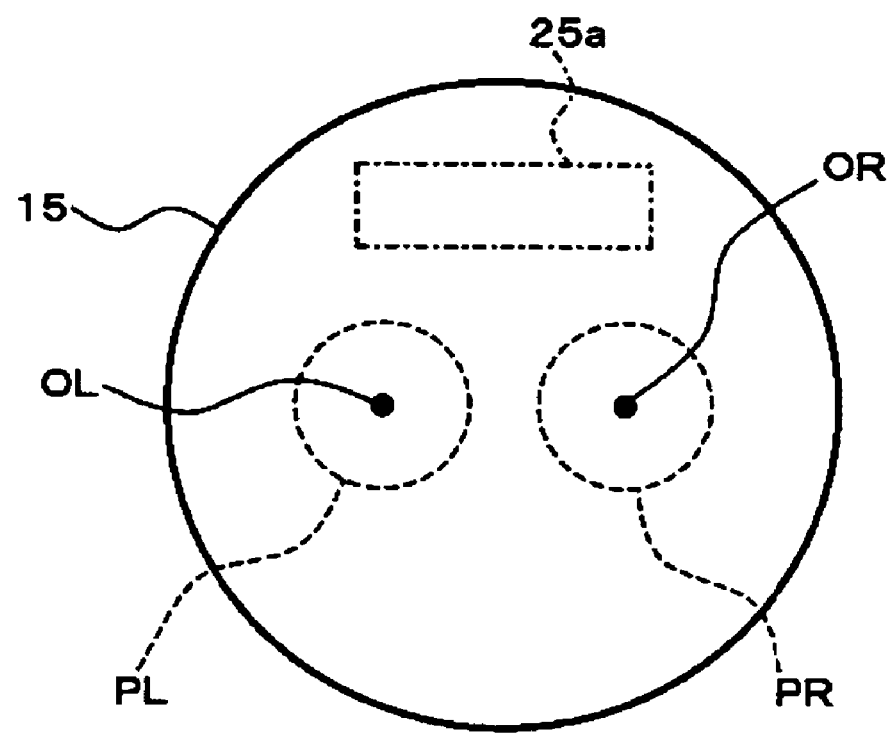
FIG. 6 is a schematic explanation view illustrating an example of the configuration of the optical system of the embodiment of the surgical microscope apparatus according to the present invention.

FIG. 6 shows the shape of an exit pupil of the illumination optical system 20 and the shapes of entrance pupils of the observation optical systems 30 as well as the positional relationship thereof viewed from above the observation optical systems 30. The bottom side of this figure is the operator side.

The exit pupil of the illumination optical system 20 is formed on the reflecting face 25a of the illumination prism 25. The exit pupil 25a (identified as the reflecting face 25a) is formed at a position opposite to the operator side across the observation optical systems 30L and 30R. Moreover, the shape of the exit pupil 25a is rectangular with a direction connecting the right and left observation optical axis OL and OR (a horizontal direction in FIG. 6) as the longitudinal direction. The shape of the exit pupil 25a corresponds to the shape of the slit hole 24a.

The entrance pupil PL of the left observation optical system 30L is formed at a position between the objective lens 15 and the zoom lens system 31 of the left observation optical system 30L as shown in FIG. 4. Similarly, the entrance pupil PR of the right observation optical system 30R is formed at a position between the objective lens 15 and the zoom lens system 31 of the right observation optical system 30R. The entrance pupils PL and PR of the right and left observation optical systems 30L and 30R are formed around the observation optical axes OL and OR, respectively, as shown in FIG. 6.

[Configuration of Control System]

Figure 7:
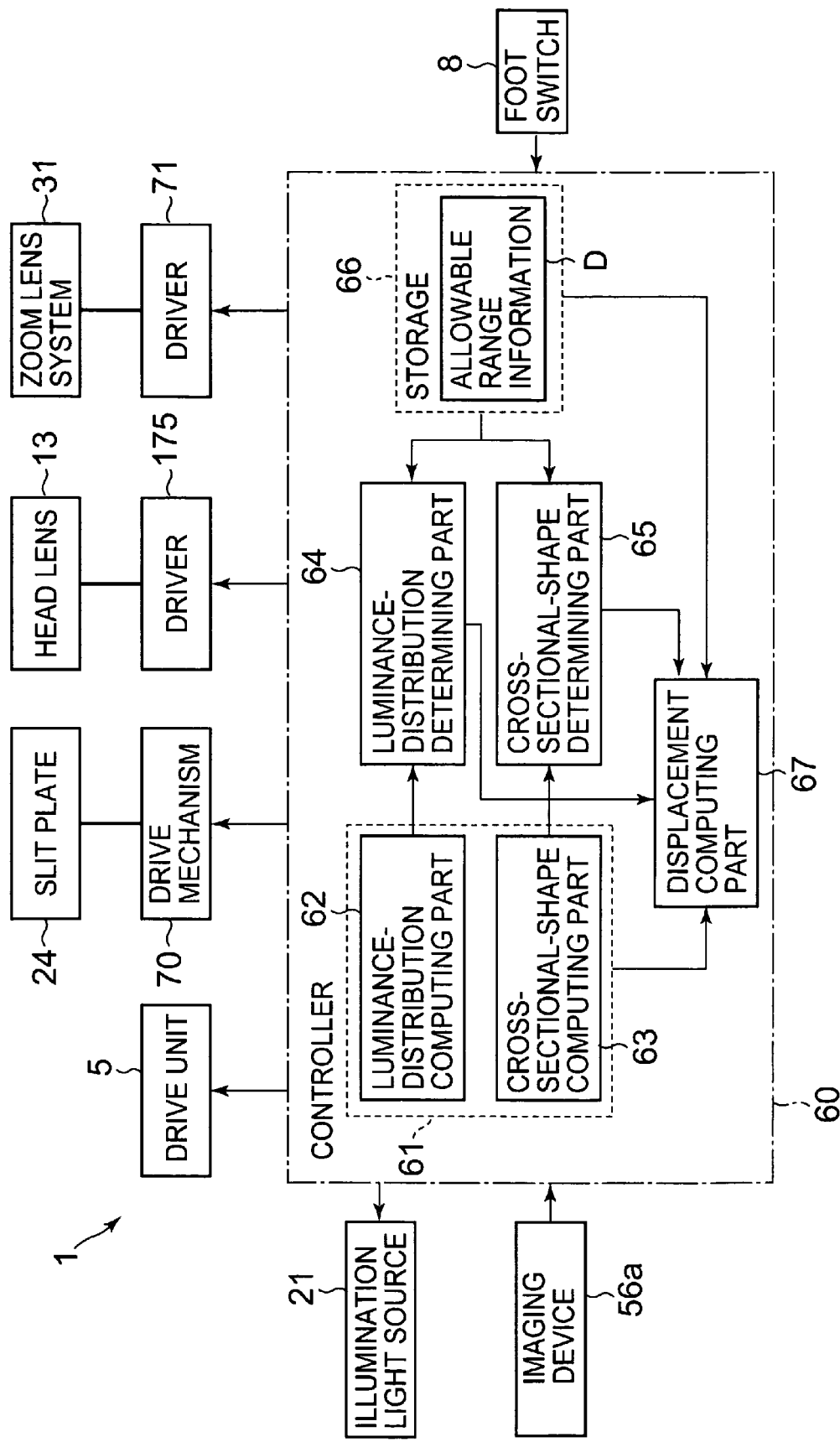
FIG. 7 is a schematic block diagram illustrating an example of the configuration of a control system of the embodiment of the surgical microscope apparatus according to the present invention.

The configuration of a control system of the surgical microscope apparatus 1 will be described. The block diagram shown in FIG. 7 shows an example of the configuration of the control system of the surgical microscope apparatus 1.

[Controller]

The control system of the surgical microscope apparatus 1 is mainly composed of a controller 60. The controller 60 controls each part of the surgical microscope apparatus 1. Moreover, the controller 60 executes various kinds of data processing.

The controller 60 may be housed in a chassis of the surgical microscope apparatus 1 (refer to FIG. 15), or may be placed outside the chassis. In the case of placing it outside the chassis, it is possible, for example, to use a computer capable of data communication with the surgical microscope apparatus 1 as the controller 60.

The controller 60 includes a microprocessor and a storage device. The microprocessor is composed of a CPU (Central Processing Unit), etc. The storage device includes a main storage device and an external storage device. The main storage device is composed of, for example, a volatile storage device such as a RAM (Random Access Memory). The external storage device is composed of, for example, a nonvolatile storage device such as a ROM (Read Only Memory) and a hard disk drive.

A computer program and data for controlling the surgical microscope apparatus 1 are previously stored in the nonvolatile storage device. Moreover, when the surgical microscope apparatus 1 is being used, various kinds of data are stored in the storage device. The microprocessor controls the surgical microscope apparatus 1 based on the computer program and data.

The controller 60 controls the lighting-up/lighting-out of the illumination light source 21. Furthermore, the controller 60 controls the illumination light source 21 to change the output light amount of the illumination light.

The imaging device 56a captures an image of the eye E and inputs the captured image data into the controller 60. Light-detecting elements are arranged on the light-receiving face of the imaging device 56a. The captured image data includes a detected value (detected intensity, etc.) by each of the light-detecting elements, information showing an arrangement position of each of the light-detecting elements (a coordinate value, etc.), and so on. Moreover, the controller 60 controls the operation of the imaging device 56a. An object to be controlled is, for example, a charge storage time and a frame rate.

The controller 60 can transmit the image captured by the imaging device 56a to a computer, a display device and a storage device, which are externally placed. These external devices display and/or store this captured image.

Moreover, the controller 60 controls drive systems of the surgical microscope apparatus 1, such as the drive unit 5, a drive mechanism 70 and the drivers 71 and 175, respectively. Here, the drive unit 5 3-dimensionally moves the operator's microscope 6 and the assistant's microscope 7. In particular, the drive unit 5 moves the operator's microscope 6, etc., in a direction orthogonal to the optical axis O of the objective lens 15 (i.e., the horizontal direction, the anteroposterior direction). The drive mechanism 70 rotates the slit plate 24 to selectively position the slit holes 24a1-24a3 on the illumination optical axis O'. The driver 71 drives the zoom lens system 31 to change the zoom magnification. The driver 175 moves the head lens 13 in the direction of the optical axis O of the objective lens 15. These drive systems include actuators and transmission mechanisms (gears, etc.), as in a conventional system.

When the foot switch 8 is operated, a signal according to the operation content is inputted into the controller 60. The controller 60 controls the surgical microscope apparatus 1 to execute an operation according to the operation content based on this signal. For example, when an operation to move the operators microscope 6 or the like is performed, the controller 60 controls the drive unit 5. Moreover, when an operation to change the zoom magnification is performed, the controller 60 controls the driver 71.

The controller 60 includes an observation-light analyzer 61, a luminance-distribution determining part 64, a cross-sectional-shape determining part 65, a storage 66, and a displacement computing part 67. The observation-light analyzer 61 includes a luminance-distribution computing part 62 and a cross-sectional-shape computing part 63.

(Observation-Light Analyzer)

The observation-light analyzer 61 obtains information showing the morphology of observation light (morphology information), based on the result of detection of reflected light (observation light) of illumination light on the eye E. The observation light is detected by the imaging device 56a. The observation-light analyzer 61 obtains the morphology information by analyzing a signal inputted from the imaging device 56a. In this embodiment, two types of morphology information (luminance distribution, cross-sectional shape) are described, but it may be constituted to use one of these types.

(Luminance-Distribution Computing Part)

The luminance-distribution computing part 62 obtains a luminance distribution of the observation light as an example of the morphology information. As described above, when the imaging device 56a detects the observation light, imaging data including the detected value by each of the light-detecting elements and the coordinate value of each of the light-detecting elements are inputted into the controller 60. The luminance-distribution computing part 62 generates a luminance image based on the detected values and the coordinate values. This processing can be performed in a conventional manner. This luminance image expresses the luminance distribution of the observation light, i.e., light intensity distribution on a cross-section of the observation light.

The luminance distribution obtained by the luminance-distribution computing part 62 may be a 1-dimensional distribution or may be a 2-dimensional distribution.

If a 1-dimensional luminance distribution is obtained, the luminance-distribution computing part 62 specifies a 1-dimensional region (e.g., linear region) on the light reception face of the imaging device 56a based on the coordinate values of the light-detecting elements. The luminance-distribution computing part 62 then obtains a 1-dimensional luminance distribution based on the detected value of each of the light-detecting elements included in this 1-dimensional region.

Figure 8:
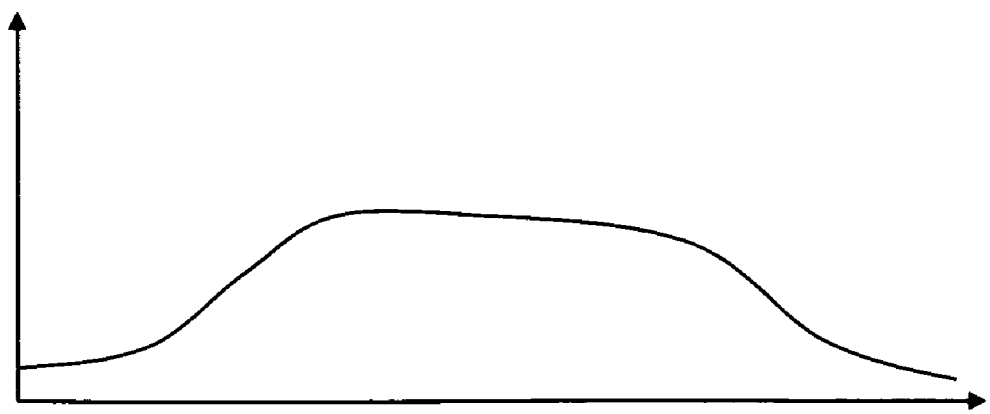
FIG. 8 is a schematic view illustrating an example of a luminance distribution of observation light in the embodiment of the surgical microscope apparatus according to the present invention.

A specific example of the 1-dimensional luminance distribution with the observation light is shown in FIG. 8. In the graph shown in FIG. 8, the horizontal axis indicates the position in the 1-dimensional region and the vertical axis indicates the luminance value.

A region specified as the 1-dimensional region may always be the same or may be different at each time of detection. In the former case, for example, a region on a line segment of a specified length that passes through the central position of the reception face can be constituted so as to be specified. On the other hand, in the latter case, for example, a light-detecting element with a maximum detected value in a 2-dimensional reception face can be constituted to be specified in order to specify a region on a ling segment of a specific length that passes through the light-detecting element. Moreover, the abovementioned 2-dimensional luminance image may be formed firstly and a pixel with a maximum luminance value in this luminance image may be specified in order to use a region on a line segment of a specific length that passes through this pixel as the abovementioned 1-dimensional region.

If a 2-dimensional luminance distribution is obtained, the luminance-distribution computing part 62 obtains the abovementioned 2-dimensional luminance image. A 2-dimensional partial region in this luminance image may be extracted in order to use it for subsequent processing. Moreover, it is possible to constitute to determine a 2-dimensional partial region on the reception face of the imaging device 56a in order to generate a luminance image in this partial region.

If only the luminance distribution of the observation light is used as the morphology information and only the 1-dimensional luminance distribution is used, an imaging device (line sensor) with light-detecting elements arranged 1-dimensionally can be used as the imaging device 56a.

(Cross-Sectional-Shape Computing Part)

The cross-sectional-shape computing part 63 obtains a cross-sectional shape of the observation light as an example of the morphology information. Here, the cross-sectional shape of the observation light indicates a shape of a light flux on a cross-section orthogonal to the traveling direction of the observation light.

The cross-sectional-shape computing part 63 obtains the cross-sectional shape of the observation light, for example, in the following manner. Firstly, the cross-sectional-shape computing part 63 generates a 2-dimensional luminance image, similarly to the luminance-distribution computing part 62.

Next, the cross-sectional-shape computing part 63, in this luminance image (frame), specifies a border of an image region showing the observation light (observation light region). This processing can be performed by threshold processing, etc. As a more specific example, a pixel with a maximum luminance in the luminance image is firstly specified and a threshold value is set based on this maximum luminance value. As this threshold value, for example, a value of a specified percentage (⅕₀, etc.) of the maximum luminance value can be set. Subsequently, pixels to form the luminance image are divided into pixels with a luminance value that exceeds such threshold value and pixels with a luminance value that is equal to such threshold value or less in order to specify the border of the observation light region.

Instead of thus setting the threshold value based on the maximum luminance value, it is also possible to use a previously set threshold value. For example, it is possible to use a luminance value 0 as the threshold value. That is, it is possible to configure to divide pixels into pixels with luminance value of 0 and pixels with luminance value of more than 0 to specify the border of the latter. The method for obtaining the cross-sectional shape of observation light is not limited to the above technique, and any technique such as known image-processing techniques can be applied.

Figure 9:
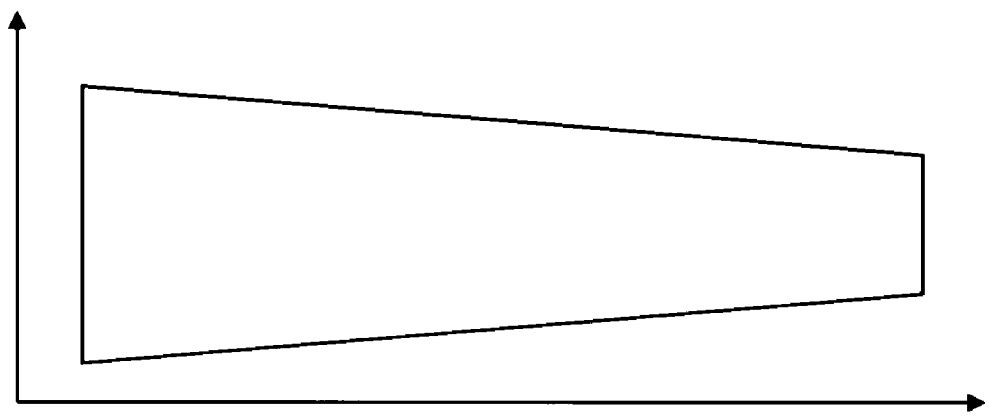
FIG. 9 is a schematic view illustrating an example of a cross-sectional shape of observation light in the embodiment of the surgical microscope apparatus according to the present invention.

A specific example of the cross-sectional shape of the observation light acquired by the cross-sectional-shape computing part 63 is shown in FIG. 9. Because the cross-sectional shape of the illumination light is rectangular due to the action of the slit plate 24, the cross-sectional shape of the observation light is a rectangle or a distorted rectangle like a trapezoid (described later). The horizontal axis and the vertical axis shown in FIG. 9 represent a plane region corresponding to the light reception face of the imaging device 56a (or a frame of the 2-dimensional luminance image).

(Storage)

The storage 66 stores various kinds of data used for a process executed by the controller 60. In particular, in the storage 66, allowable range information D is previously stored. Below, the allowable range information D will be described. The storage 66 is an example of the "storage" of the present invention.

As described above, the cross-sectional shape of the illumination light projected onto the eye E is rectangular due to the slit plate 24. Moreover, the luminance distribution in this rectangular cross-section is almost uniform. Therefore, if the positional relationship of the optical system with respect to the eye E is appropriate, the cross-sectional shape of the observation light, which is the reflected light of the illumination light on the eye E, is almost rectangular and the luminance distribution in the cross-section is almost uniform. In this embodiment, the reflected light of the illumination light on the surface of the cornea Ec or the reflected light on the surface that is positioned only ½ of the corneal curvature radius deeper from the corneal apex is considered (corresponding to the position of the imaging device 56a).

The allowable range information D shows an allowable range when an ideal morphology of the observation light is the reference. The allowable range information D of this embodiment includes allowable range information on the luminance distribution (luminance-distribution allowable range information) and allowable range information on the cross-sectional shape (cross-sectional-shape allowable range information).

The luminance-distribution allowable range information is set based on the profile of luminance distribution to become the reference (reference distribution profile). The reference distribution profile is set to a shape corresponding to the shape (rectangle) of the cross-section of the illumination light. The reference distribution profile is an example of the "specified reference pattern" of the present invention.

Figure 10:
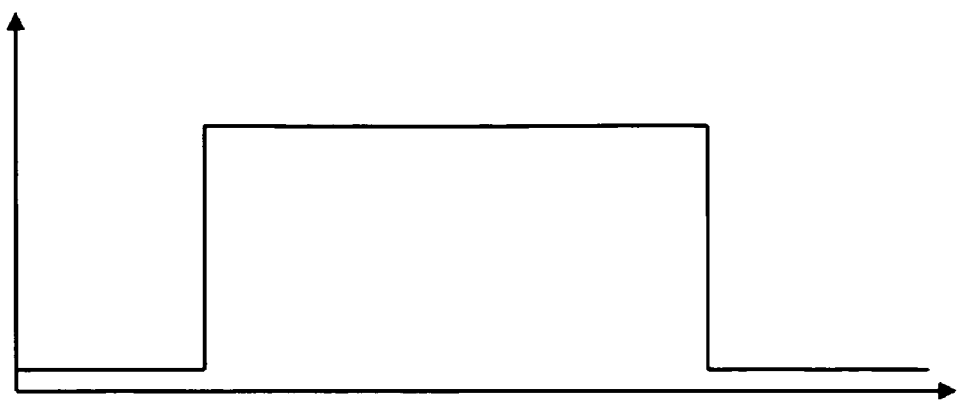
FIG. 10 is a schematic view illustrating an example of a reference distribution profile of observation light in the embodiment of the surgical microscope apparatus according to the present invention.

If a 1-dimensional luminance distribution is used, the reference distribution profile is shaped like a 1-dimensional rectangular pulse as shown in FIG. 10. The rectangular pulse is a shape that takes a first value in a specified connected region within a domain and takes a second value in a region around the connected region. The luminance-distribution allowable range information defines an allowable range of a difference in shape from this rectangular pulse. The definitional content includes an allowable range of the height of the pulse, an allowable range of the corner radius of the rectangle, an allowable range of the width of the pulse, etc.

If a 2-dimensional luminance distribution is used, the reference distribution profile is shaped like a 2-dimensional rectangular pulse (not shown). That is, the 2-dimensional luminance distribution is binary data with a 2-dimensional plane as the domain, and has a shape formed by a top composed of a rectangular plane and a planate bottom positioned therearound.

The luminance-distribution allowable range information defines an allowable range of a difference in shape from this 2-dimensional rectangular pulse. The definitional content is the same as in the case of the 1-dimension.

Figure 11:
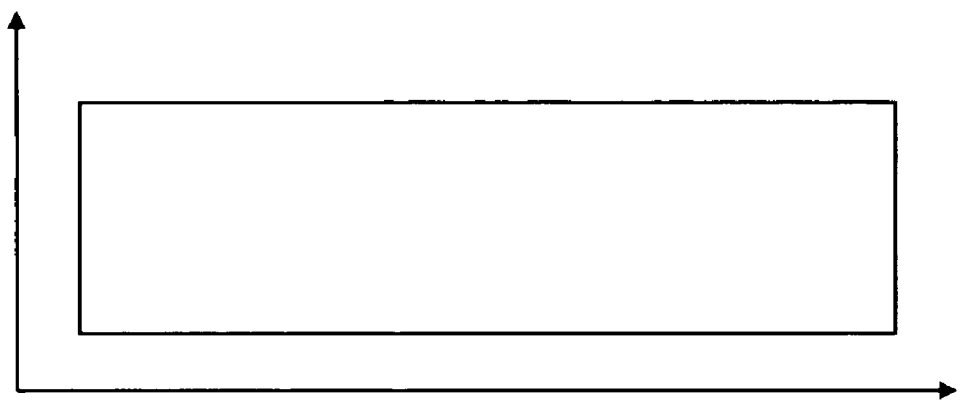
FIG. 11 is a schematic view illustrating an example of a reference cross-sectional shape of observation light in the embodiment of the surgical microscope apparatus according to the present invention.

The cross-sectional-shape allowable range information is set based on a cross-sectional shape to become the reference (reference cross-sectional shape). The reference cross-sectional shape is set to a shape corresponding to the shape of the cross-section of the illumination light (a rectangle). The reference cross-sectional shape can be set, for example, to a shape similar to a rectangle, which is the cross-sectional shape of the illumination light. The reference cross-sectional shape is an example of the "specified reference pattern" of the present invention. An example of the reference cross-sectional shape is shown in FIG. 11.

The cross-sectional-shape allowable range information defines an allowable range of a difference in shape from the reference cross-sectional shape. The definitional content includes an allowable range of the ratio of lengths in the longitudinal direction and the widthwise direction, an allowable range of the distortion in the longitudinal direction and the widthwise direction, etc.

In a case where the processing is performed based on a morphology of the observation light other than the above-mentioned, allowable range information according to the morphology is previously stored in the storage 66.

(Luminance-Distribution Determining Part)

The luminance-distribution determining part 64 determines adequacy of the luminance distribution of the observation light acquired by the luminance-distribution computing part 62. More specifically, the luminance-distribution determining part 64 determines whether the luminance distribution of the observation light is within the allowable range shown in the allowable range information D. This process can be executed by comparing the profile of the luminance distribution of the observation light with the allowable range shown in the luminance-distribution allowable range information. The luminance-distribution determining part 64 is an example of the "determining part" of the present invention.

(Cross-Sectional-Shape Determining Part)

The cross-sectional-shape determining part 65 determines adequacy of the cross-sectional shape of the observation light acquired by the cross-sectional-shape computing part 63. More specifically, the cross-sectional-shape determining part 65 determines whether the cross-sectional shape of the observation light is within the allowable range shown in the allowable range information D. This process can be executed by comparing the cross-sectional shape of the observation light with the allowable range shown in the cross-sectional-shape allowable range information. The cross-sectional-shape determining part 65 is an example of the "determining part" of the present invention.

The luminance-distribution determining part 64 and the cross-sectional-shape determining part 65 may execute a determination process as described below. The process by the luminance-distribution determining part 64 will be described below (the process by the cross-sectional-shape determining part 65 is similar).

The luminance-distribution determining part 64 firstly compares the luminance distribution profile of the observation light acquired by the luminance-distribution computing part 62 with the reference distribution profile, and computes a correlation coefficient thereof. It is possible to compute this correlation coefficient by, for example, considering a correlation when the both are regarded as images (image correlation) or a correlation when the both are regarded as graphs. Then, the luminance-distribution determining part 64 determines whether this correlation coefficient is within a specified allowable range.

In this example, the allowable range of the correlation coefficient is previously set and stored in the storage 66 as the allowable range information D. In addition, information that shows the reference distribution profile is also previously stored in the storage 66.

(Displacement Computing Part)

The displacement computing part 67 computes a displacement of the head lens 13 when the luminance distribution of the observation light is determined to be improper by the luminance-distribution determining part 64. The displacement of the head lens 13 is a displacement in a direction along the optical axis O of the objective lens 15. Moreover, this displacement is a vector amount that includes a displacement direction and a displacement amount. This displacement direction and this displacement amount correspond to a movement direction and a movement amount of the head lens 13 by the controller 60, respectively.

Moreover, the displacement computing part 67 computes a displacement of the optical system (the illumination optical system 20, the observation optical systems 30, and the head lens 13) when the cross-sectional shape of the observation light is determined to be improper by the cross-sectional-shape determining part 65. The displacement of the optical system is a displacement in a direction orthogonal to the optical axis O of the objective lens 15. Moreover, this displacement is a vector amount that includes a displacement direction and a displacement amount. This displacement direction and this displacement amount correspond to a movement direction and a movement amount of the optical system by the controller 60, respectively.

The displacement computing part 67 refers to, for example, the morphology information acquired by the observation-light analyzer 61 and the information stored in the storage 66 in order to execute the abovementioned computing process. The reference information stored in the storage 66 includes the allowable range information D and other information. As an example, the displacement computing part 67 obtains a departure between the morphology information and the allowable range information D, and obtains a displacement based on this departure. The process executed by the displacement computing part 67 will be described with specific examples in a second embodiment and modification described above.

[Operation]

Figure 12:
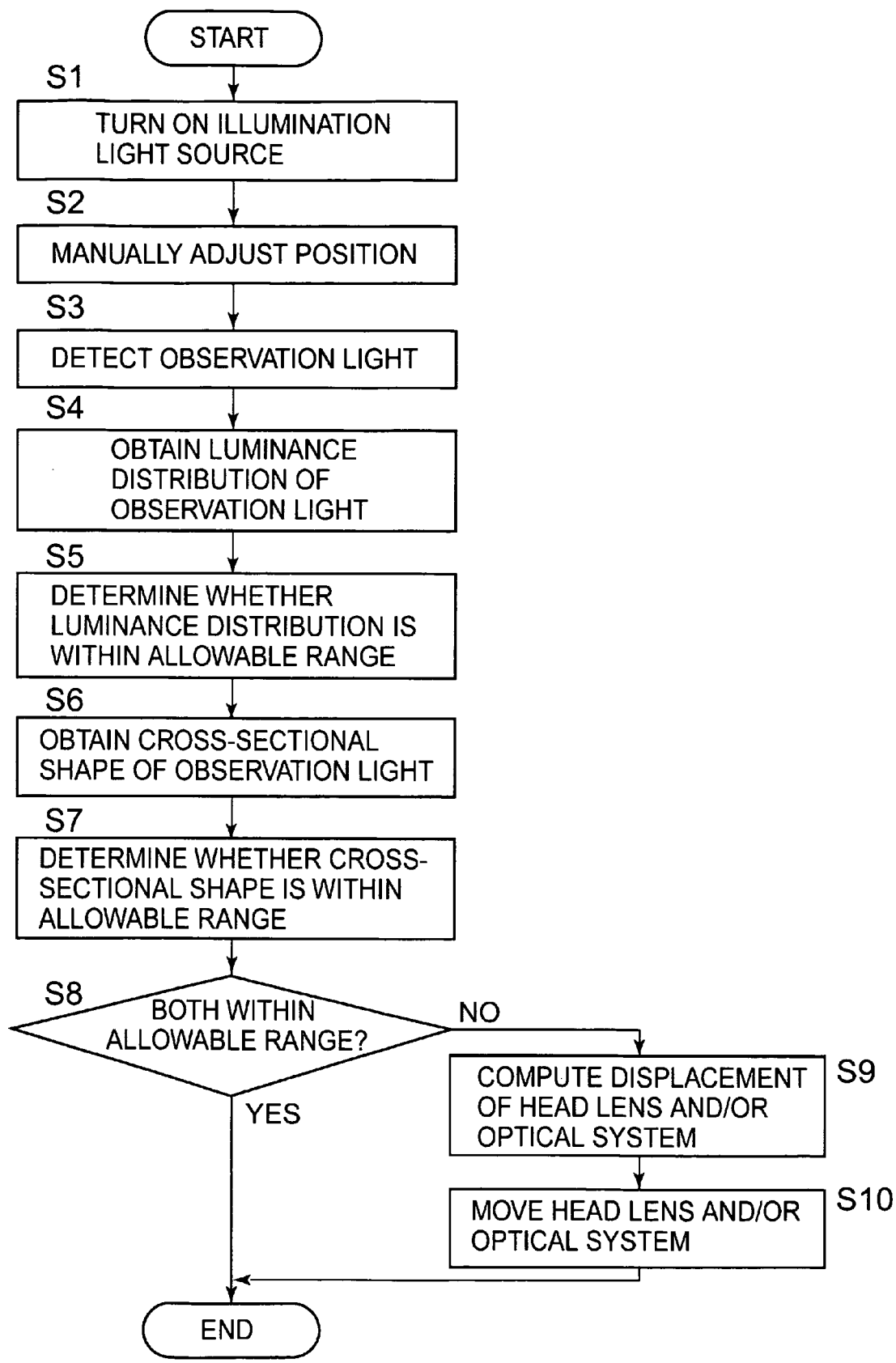
FIG. 12 is a flowchart illustrating an example of the operation of the embodiment of the surgical microscope apparatus according to the present invention.

The operation of the surgical microscope apparatus 1 will now be described. A flowchart shown in FIG. 12 shows an example of the operation of the surgical microscope apparatus 1 regarding position adjustment of the optical system with respect to the eye E.

A patient lies on his/her back on a surgical bed. Firstly, an operator turns on the illumination light source 21 by operating the foot switch 8, etc. (S1). It is assumed that at this moment, one of the slit holes 24a1-24a3 of the slit plate 24 is positioned on the illumination optical axis O'(selectable as necessary). The shape of each of the slit holes 24a1-24a3 is rectangular as described above. It is assumed that the head lens 13 is positioned at a usage position.

Next, position adjustment of the optical system with respect to the eye E is executed manually (S2). To be specific, the operator (operator, assistant, etc.) firstly moves the lens barrel part 10 above the eye E and adjusts the position of the lens barrel part 10 so that illumination light is projected onto the cornea Ec. The optical axis O of the objective lens 15 is positioned in the vertical direction.

At this moment, a projection image of the illumination light is formed on the cornea Ec. This projection image generally has a distorted rectangle. The imaging device 56a detects this projection image (corneal reflection light of the illumination light: observation light) (S3). The imaging device 56a inputs imaging data that shows the detection results of the observation light, into the controller 60.

The luminance-distribution computing part 62 obtains the luminance distribution of the observation light based on this imaging data (S4). The luminance-distribution determining part 64 determines whether this luminance distribution of the observation light is within the allowable range based on the luminance distribution and the allowable range information D (luminance-distribution allowable range information) (S5).

Moreover, the cross-sectional-shape computing part 63 obtains the cross-sectional shape of the observation light based on the imaging data acquired in Step 3 (S6). The cross-sectional-shape determining part 65 determines whether this cross-sectional shape of the observation light is within the allowable range based on the cross-sectional shape and the allowable range information D (cross-sectional-shape allowable range information) (S7).

Processing on the cross-sectional shape may be executed before the processing on the luminance distribution. Moreover, these processing may be executed in parallel.

Subsequently, in a case where the determination results in Step 5 and Step 7 show that the both are within the allowable ranges (S8:Y), there is no need to move the head lens 13 or the optical system, and the process of position adjustment of the optical system with respect to the eye E is ended.

On the other hand, in a case where either of or both of the luminance distribution and the cross-sectional shape of the observation light are determined to be out of the allowable range (S8: N), the displacement computing part 67 computes a displacement that corresponds to the information determined to be out of the allowable range (S9).

Specifically, in a case where the luminance distribution is determined to be out of the allowable range in Step 5, the displacement computing part 67 computes the displacement between the position that corresponds to the reference distribution profile (a head-lens reference position) and the current position of the head lens 13. In a case where the cross-sectional shape is determined to be out of the allowable range in Step 7, the displacement computing part 67 computes the displacement between the position that corresponds to the reference cross-sectional shape (an optical-system reference position) and the current position of the optical system.

The controller 60 controls the driver 175 and/or the drive unit 5 based on the displacement of the head lens 13 alone and/or the displacement of the optical system acquired in Step 9 so as to move the head lens 13 and/or the optical system (S10).

That is, in a case where the displacement of the head lens 13 is computed in Step 9, the controller 60 controls the driver 175 so as to move the head lens 13 in the movement direction that corresponds to the displacement by the movement amount that corresponds to the displacement. Moreover, in a case where the displacement of the optical system is computed in Step 9, the controller 60 controls the drive unit 5 so as to move the optical system in the movement direction that corresponds to the displacement by the movement amount that corresponds to the displacement. This is the end of the process of the position adjustment of the optical system with respect to the eye E.

[Action and Advantageous Effect]

Action and advantageous effects of the surgical microscope apparatus 1 will now be described.

The surgical microscope apparatus 1 has a driver configured to move the optical system including the illumination optical system 20, the observation optical systems 30 and the head lens 13. As the driver, the drive unit 5 and the driver 175 are disposed. The drive unit 5 3-dimensionally moves the entire optical system, and particularly, moves the optical system in the horizontal direction (a direction orthogonal to the optical axis O of the objective lens 15). The driver 175 moves only the head lens 13 in the vertical direction (a direction along the optical axis O).

Moreover, the surgical microscope apparatus 1 has the imaging device 56a configured to detect the reflected light (observation light) of the illumination light guided by the observation optical systems 30. The imaging device 56a functions as an example of the "detector" of the present invention.

In addition, the surgical microscope apparatus 1 comprises the controller 60 configured to control the driver based on the result of detection of the observation light by the imaging device 56a and change the relative position of the optical system with respect to the eye E. The controller 60 functions as an example of the "controller" of the present invention.

Such surgical microscope apparatus 1 is configured to automatically execute the position adjustment of the optical system with respect to the eye E (including a case only with the head lens 13). Therefore, it is possible to simplify the operation for adjusting the positional relationship between the eye E and the optical system.

In particular, as shown in the flowchart of FIG. 12, it is possible to automatically perform precise positional adjustment only by manually performing a rough positional adjustment.

Consequently, it is possible to easily prevent a situation where flare occurs within the observation field. Moreover, even if the position of the eye E changes, it is possible to easily execute the position adjustment of the optical system with respect to the eye E. In addition, the following effects can be expected: concentration on surgery without taking time on the position adjustment; easy operation; prevention of lengthening of surgery; and easy position adjustment even by a not-expert person.

In order to obtain such action and advantageous effects, the illumination optical system 20 projects light having a cross-section of a specified shape (in this embodiment, rectangle) onto the eye E as the illumination light. The observation-light analyzer 61 of the controller 60 then obtains morphology information that shows the morphology of this observation light based on results of the observation light detected by the imaging device 56a. The controller 60 controls the driver based on this morphology information.

The morphology information includes the luminance distribution and/or the cross-sectional shape of the observation light. The luminance distribution is used to position the head lens 13 in a vertical direction. Moreover, the cross-sectional shape is used to position the optical system in a horizontal direction. Furthermore, the observation-light analyzer 61 functions as an example of the "analyzer" of the present invention.

Second Embodiment

A second embodiment of the surgical microscope apparatus according to the present invention will now be described. In this embodiment, a method for computing a displacement of the optical system is particularly described in detail. The method of computing a displacement described below can also be applied to the abovementioned first embodiment (the displacement computing part 67).

[Configuration]

Figure 13:
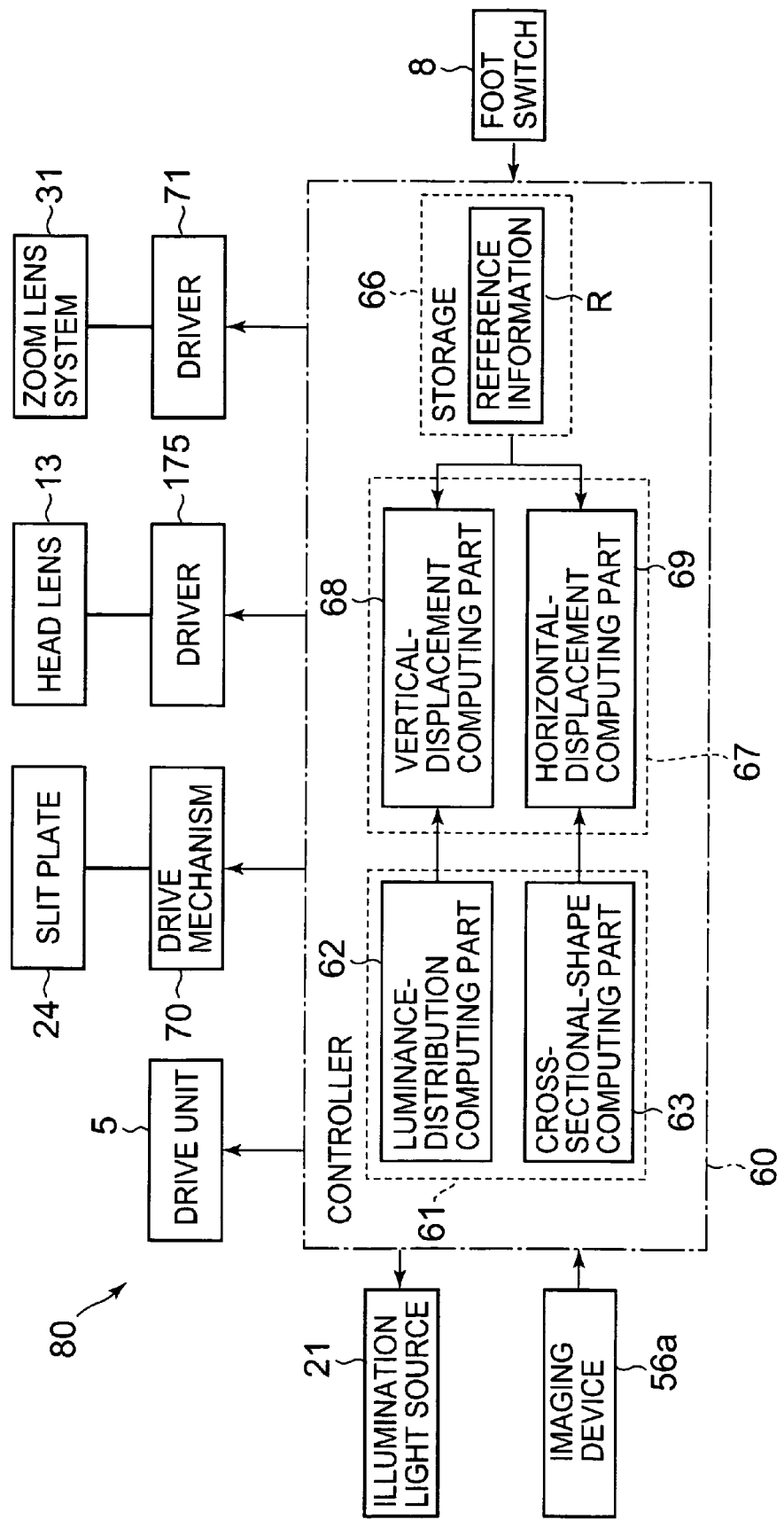
FIG. 13 is a schematic block diagram illustrating an example of the configuration of a control system of an embodiment of the surgical microscope apparatus according to the present invention.

The surgical microscope apparatus according to this embodiment has an optical system similar to the surgical microscope apparatus 1 of the first embodiment (refer to FIG. 1 through FIG. 6). This optical system includes the illumination optical system 20, the observation optical systems 30, and the head lens 13. In particular, the surgical microscope apparatus of the present embodiment projects an illumination light having a cross-section of a specified shape (rectangle) onto an eye, as in the first embodiment. FIG. 13 shows an example of the configuration of a control system of the surgical microscope apparatus of this embodiment. Similar components to those of the first embodiment will be denoted by the same reference symbols below.

[Controller]

A surgical microscope apparatus 80 shown in FIG. 13 has the controller 60 similar to that of the first embodiment. The controller 60 of this embodiment includes the observation-light analyzer 61, the storage 66, and the displacement computing part 67.

The observation-light analyzer 61 includes the luminance-distribution computing part 62 and the cross-sectional-shape computing part 63, similarly to that of the first embodiment. Reference information R is previously stored in the storage 66. The displacement computing part 67 is provided with a vertical-displacement computing part 68 and a horizontal-displacement computing part 69.

(Reference Information)

The reference information R is used in a process to compute a displacement of the optical system. The reference information R includes vertical-displacement reference information and horizontal-displacement reference information. The vertical-displacement reference information is referred to in the process for computing a displacement in the vertical direction of the head lens 13 (direction of the optical axis O of the objective lens 15). The horizontal-displacement reference information is referred in the processing for computing a displacement in the horizontal direction of the optical system (direction orthogonal to the optical axis O).

The vertical-displacement reference information is information, for example, to correlate the luminance distribution profile of the observation light with a displacement in the vertical direction of the head lens 13.

A specific example of this vertical-displacement reference information will now be described. In a state in which the distance between the head lens 13 and the cornea Ec is proper (a state in which the illumination light is appropriately focused on the cornea Ec), the luminance distribution of the observation light is (almost) rectangularly pulsed (reference distribution profile) as shown in FIG. 10. On the other hand, in a state where this distance is not proper, the luminance distribution of the observation light is a shape such that a rectangular pulse is distorted as shown in FIG. 8.

The luminance distribution profile changes according to a departure from the proper distance. In particular, when the distance is not proper, the maximum value of luminance is lower than in a case where the distance is proper, for a reason that the projection image of the illumination light at the cornea enlarges and part of the corneal reflection light does not return to the head lens 13 (i.e., the maximum value of the luminance distribution is lower than the maximum value of the reference distribution profile). Moreover, for a similar reason, the light amount of the observation light is smaller than when the distance is proper (i.e., the integration value of the graph of the luminance distribution is lower than the integration value of the graph of the reference distribution profile).

The relationship between the profile of the luminance distribution and the displacement of the head lens 13 (vertical-displacement reference information) can be obtained theoretically, or can be obtained by actual measurement. In a specific example of obtaining it theoretically, it is possible to obtain the relationship between the profile of the luminance distribution and the displacement of the head lens 13 by assuming a general value of the corneal curvature and executing simulations (e.g., ray tracing) on various distances between the cornea and the head lens. At this moment, it is also possible to execute similar simulations on various values of the corneal curvature, respectively. In this case, it is possible to selectively refer to the vertical-displacement reference information according to the corneal curvature (known) of the eye E.

On the other hand, in a specific example of obtaining by actual measurement, it is possible to obtain the relationship between the profile of the luminance distribution and the displacement of the head lens 13 from a measured value using a Gullstrand's eye model, or it is possible to obtain clinically using human eyes.

Next, the horizontal-displacement reference information will be described. The horizontal-displacement reference information is, for example, information that correlates the cross-sectional shape of the observation light with the displacement of the optical system in the horizontal direction with respect to the cornea Ec. This displacement is, for example, a displacement with respect to the apical position of the cornea Ec.

A specific example of this horizontal-displacement reference information will now be described. In a state where the position of the optical system in the horizontal direction with respect to the cornea Ec is proper (a state where the optical axis O of the objective lens 15 is consistent with the corneal apex), the cross-sectional shape of the observation light is a (substantially) rectangular shape (a reference cross-sectional shape) as shown in FIG. 11. On the other hand, in a state where this position is not proper, the cross-sectional shape of the observation light is a shape like a distorted rectangle as shown in FIG. 9.

The cross-sectional shape of the observation light changes in accordance with a deviation from the proper position. In particular, in a case where the position is not proper, the lengths of two sides facing each other in the distortion direction are different.

For example, FIG. 9 shows the morphology of the cross-section in the horizontal direction. In this case, when a side on the left (on the vertical-axis side) is compared with a side on the right, the side on the left is longer than the side on the right. This is because the projection position of the illumination light deviates in the horizontal direction with respect to the corneal apex position.

At this moment, the direction of deviation with respect to the corneal apex position (in this case, rightward or leftward) is determined based on whether light heading to the cornea Ec from the head lens 13 is converging light or diverging light (because the corneal apex position is positioned the highest and, the farther a distance therefrom is, the lower it is positioned). In the case of converging light, the projection position of the illumination light deviates in the direction of the shorter side (in FIG. 9, it deviates rightward). On the other hand, in the case of diverging light, the projection position of the illumination light deviates in the direction of the longer side (in FIG. 9, it deviates leftward). The same is true of a deviation in the front-rear direction (anteroposterior direction). In general, the illumination light heading to the cornea Ec from the head lens 13 is converging light.

The deviation of the projection position of the illumination light results from the displacement of the optical system (the optical axis O) in the horizontal direction. Therefore, the cross-sectional shape of the observation light and the displacement direction of the optical system in the horizontal direction are correlated.

In addition, the amount of displacement of the optical system in the horizontal direction is also reflected in the cross-sectional shape of the observation light. That is, considering the shape of the cornea Ec, it is clear that the more the projection position of the illumination light deviates from the corneal apex position, the more the cross-sectional shape of the observation light is distorted.

The degree of the distortion can be evaluated by, for example, comparing the lengths of the two facing sides. Specifically, it is possible to evaluate the amount of displacement of the optical system in the right-left direction (horizontal direction) by comparing the length of the right side with the length of the left side. Moreover, it is possible to evaluate the amount of displacement of the optical system in the front-rear direction by comparing the length of the upper side with the length of the lower side. In an example of the evaluation method, it is possible to evaluate by the ratio of the lengths of the two facing sides.

Moreover, it is also possible to evaluate the degree of the distortion of the cross-sectional shape of the observation light based on the lengths of the sides. Specifically, in a case where a certain zoom magnification is applied, the lengths of the sides when the displacement of the optical system is zero are previously acquired, and the relationship between the displacement of the optical system and the lengths of the sides are previously acquired.

The relationship between the cross-sectional shape of the observation light and the displacement of the optical system (the horizontal-displacement reference information) as described above can be obtained theoretically or can be obtained by actual measurement as in the case of the vertical-displacement reference information.

(Displacement Computing Part)

The displacement computing part 67 computes a displacement of the head lens 13 and a displacement of the optical system. The displacement computing part 67 is an example of the "computing part" of the present invention. It is provided with the vertical-displacement computing part 68 and the horizontal-displacement computing part 69.

(Vertical-Displacement Computing Part)

The vertical-displacement computing part 68 obtains a displacement of the head lens 13 based on the luminance distribution of the observation light. This displacement is equivalent to a movement direction and a movement amount of the head lens 13.

Into the vertical-displacement computing part 68, information on the luminance distribution of the observation light acquired by the luminance-distribution computing part 62 is inputted (refer to FIG. 8). The vertical-displacement computing part 68 refers to the vertical-displacement reference information of the reference information R to acquire the displacement of the head lens 13 in the vertical direction that corresponds to this luminance distribution.

(Horizontal-Displacement Computing Part)

The horizontal-displacement computing part 69 obtains a displacement of the optical system based on the cross-sectional shape of the observation light. This displacement is equivalent to a movement direction and a movement amount of the optical system.

Into the horizontal-displacement computing part 69, information on the cross-sectional shape of the observation light acquired by the cross-sectional-shape computing part 63 is inputted (refer to FIG. 9). The horizontal-displacement computing part 69 refers to the horizontal-displacement reference information of the reference information R to acquire the displacement of the optical system (the optical axis O) in the horizontal direction that corresponds to this cross-sectional shape.

[Operation]

Figure 14:
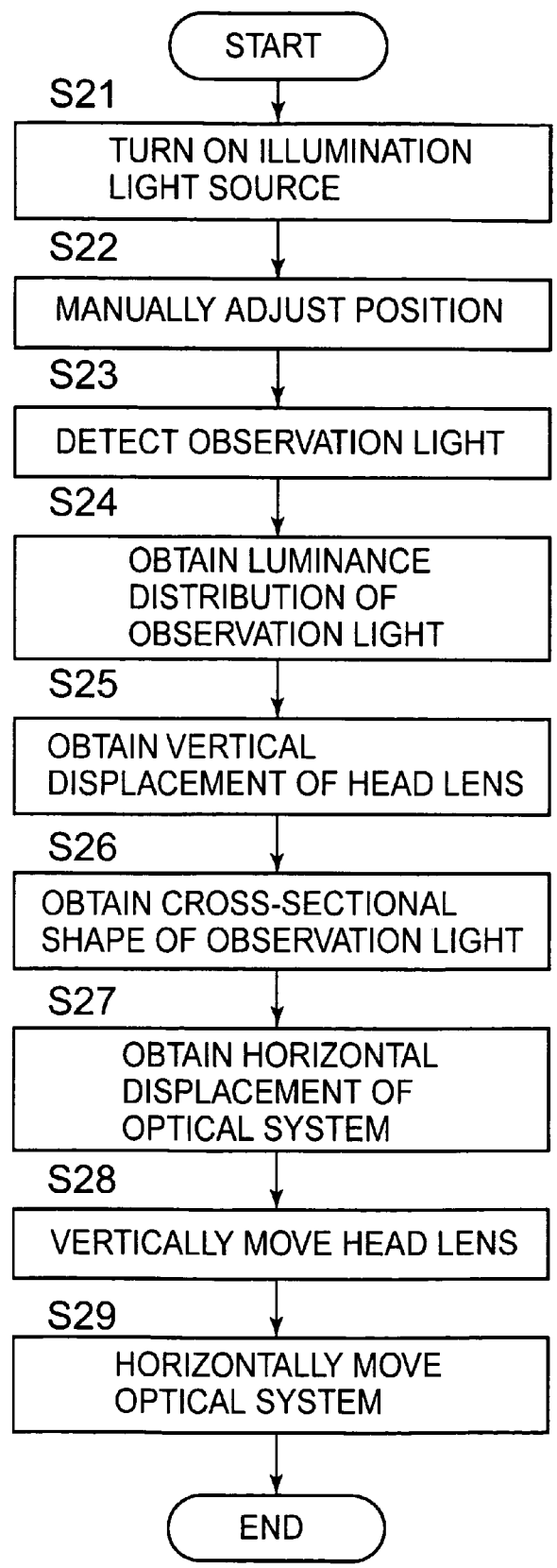
FIG. 14 is a flowchart illustrating an example of the operation of an embodiment of the surgical microscope apparatus according to the present invention.

The operation of the surgical microscope apparatus 80 will now be described. A flowchart shown in FIG. 14 shows an example of the operation of the surgical microscope apparatus 80 regarding position adjustment of the optical system with respect to the eye E.

Firstly, the illumination light source 21 is turned on by operating the foot switch 8, etc. (S21). At this moment, one of the slit holes 24a1-24a3 of the slit plate 24 is positioned on the illumination optical axis O'. Moreover, the head lens 13 is positioned at a usage position.

Next, the position adjustment of the optical system with respect to the eye E is performed manually (S22). Consequently, a projection image of the illumination light of a distorted rectangle is formed on the cornea Ec. The imaging device 56a detects this projection image (corneal reflection light of the illumination light: observation light) (S23). The imaging device 56a inputs imaging data that shows the detection results of the observation light into the controller 60.

The luminance-distribution computing part 62 obtains the luminance distribution of the observation light based on this imaging data (S24). The vertical-displacement computing part 68 computes a displacement in the vertical direction of the head lens 13 based on this luminance distribution and the reference information R (vertical-displacement reference information) (S25).

Moreover, the cross-sectional-shape computing part 63 obtains the cross-sectional shape of the observation light based on the imaging data acquired in Step 3 (S26). The horizontal-displacement computing part 69 computes a displacement in the horizontal direction of the optical system (the optical axis O) based on this cross-sectional shape and the reference information R (horizontal-displacement reference information) (S27).

Processing regarding the displacement of the optical system may be executed before the processing regarding the displacement of the head lens 13. Moreover, these processing may be executed in parallel.

The controller 60 controls the driver 175 based on the displacement acquired in Step 25 to move the head lens 13 in the movement direction corresponding to the displacement as well as in the vertical direction by the movement amount corresponding to the displacement (S27).

Moreover, the controller 60 controls the drive unit 5 based on the displacement acquired in Step 27 to move the optical system (the lens barrel part 10) in the movement direction corresponding to the displacement as well as in the horizontal direction by the movement amount corresponding to the displacement (S28).

The optical system may be moved before the head lens 13 is moved. Otherwise, the both may be moved simultaneously.

[Action and Advantageous Effect]

The surgical microscope apparatus 80 computes a displacement in the vertical direction of the head lens 13 based on the luminance distribution of the observation light, and automatically performs the position adjustment of the head lens 13 based on this displacement. At this moment, the position of the head lens 13 is changed so that the luminance distribution profile of the observation light becomes the same as (at least, becomes close to) the reference distribution profile.

Moreover, the surgical microscope apparatus 80 computes a displacement in the horizontal direction of the optical system based on the cross-sectional shape of the observation light, and automatically performs the position adjustment of the optical system based on this displacement. At this moment, the position of the optical system is changed so that the cross-sectional shape of the observation light becomes the same as (at least, becomes close to) the reference cross-sectional shape.

According to the surgical microscope apparatus 80, it is possible to easily prevent a situation where flare occurs within the observation field. Moreover, even if the position of the eye E changes, it is possible to easily perform position adjustment of the optical system with respect to the eye E. In addition, the following effects can be expected: concentration on surgery without taking time on the position adjustment; easy operation; prevention of lengthening of surgery; and easy position adjustment even by a not-expert person.

It is possible to configure to determine whether the result of displacement computing is within an allowable range and, only when it is not within the allowable range, move the head lens 13 and/or the optical system. This determination process is executed by the controller 60. Moreover, this allowable range can be set as in, for example, the first embodiment. The set allowable range is previously stored in the storage 66.

Modification

The surgical microscope apparatus described above is merely an example to implement the present invention. Thus, it is possible to apply any modification within the scope of the gist of the present invention.

[Method of Computing Displacement]

A modification of the method of computing displacements of the head lens and the optical system will now be described. Firstly, a modification of the method of computing the displacement of the head lens 13 will be described.

Firstly, as in the second embodiment (Steps 21-24), the luminance distribution of the observation light is obtained. Next, the controller 60 controls the driver 175 to move the head lens 13 in a specified direction by a specified distance. The movement direction and movement distance at this moment may be previously determined, or may be determined based on the abovementioned luminance distribution.

When the head lens 13 is moved, the imaging device 56*a* detects observation light. The luminance-distribution computing part 62 obtains the luminance distribution of this new observation light. The vertical-displacement computing part 68 compares the luminance distributions of the observation light before and after the movement of the head lens 13, and obtains a displacement of the head lens 13. This displacement is, for example, a displacement of the position of the head lens 13 after the movement thereof with respect to a proper position corresponding to the reference distribution profile.

A specific example of the method of computing the displacement will be described. Due to the movement of the head lens 13, the luminance distributions before and after the movement become different from each other. The vertical-displacement computing part 68 obtains a movement direction and movement amount of the head lens 13 necessary to shift the luminance distribution to the reference distribution profile, by comparing the movement direction and movement amount of the head lens 13 with the change of the luminance distribution corresponding thereto.

A specific example of a method of specifying the movement direction will be described. In a case where a distortion of the luminance distribution profile (a distortion with respect to the reference distribution profile) has increased due to the movement of the head lens 13, a direction opposite thereto is specified as a target movement direction. On the other hand, in a case where the distortion has decreased due to the movement of the head lens 13, the direction is specified as a target movement direction.

A specific example of a method of specifying the movement amount will be described. The movement amount of the head lens 13 is compared with the change of the luminance distribution profiles before and after the movement. Specifically, for example, the change in the maximum value of the luminance or the change in the integration value of the luminance distribution (the light amount of the observation light), etc., is compared. From the result of this comparison, it is possible to obtain a change amount (a unit change amount) of the luminance distribution profile when the head lens 13 is moved only by a specified unit distance. This process is executed by, for example, dividing the change amount of the luminance distribution profile by the movement distance of the head lens 13. At this moment, a coefficient according to the corneal curvature, etc., may be considered.

The controller 60 controls the driver 175 based on the displacement obtained as the above so as to move the head lens 13. The movement direction and the movement amount at this moment are a direction and a distance that correspond to the displacement.

In the above example, the luminance distributions of the observation light regarding the two positions of the head lens 13 are compared, but it is possible to enhance the accuracy of the position adjustment by acquiring and comparing luminance distributions regarding three or more positions.

According to this modification, it is possible to accurately perform the position adjustment of the head lens 13 in accordance with the individual eyes E.

Next, a modification of the method of computing a displacement of the optical system will be described. Firstly, a cross-sectional shape of the observation light is obtained as in the second embodiment (Steps 21-23, Step 26).

Subsequently, the controller 60 controls the drive unit 5 to move the optical system (the lens barrel part 10) in a specified direction by a specified distance. The movement direction and the distance at this moment may be previously determined or determined based on the above cross-sectional shape.

When the optical system is moved, the imaging device 56*a* detects observation light. The cross-sectional-shape computing part 63 obtains the cross-sectional shape of this new observation light. The horizontal-displacement computing part 69 compares the cross-sectional shapes of the observation light before and after the movement of the optical system to obtain a displacement of the optical system. This displacement is, for example, a displacement of the position of the optical system after the movement thereof with respect to a proper position that corresponds to the reference cross-sectional shape.

A specific example of the method of computing the displacement will now be described. Due to the movement of the optical system, the cross-sectional shapes before and after the movement thereof become different from each other. The horizontal-displacement computing part 69 obtains a movement direction and a movement amount of the optical system necessary to shift the cross-sectional shape to the reference cross-sectional shape, by comparing the movement direction and the moving distance of the optical system with the change of the cross-sectional shape that corresponds to it.

A specific example of the method of specifying the movement direction will be described. In a case where a distortion of the cross-sectional shape (a distortion with reference to the reference cross-sectional shape) has increased due to the movement of the optical system, a direction opposite thereto is specified as a target movement direction. On the other hand, in a case where a distortion has decreased due to the movement of the optical system, the direction is specified as the target movement direction. The change of the distortion can be evaluated by, for example, a change in ratio of the lengths of the two facing sides or a change in length of each of the sides.

The change of the distortion of the cross-sectional shape is individually specified for the anteroposterior direction and the horizontal direction. Therefore, due to the movement of the optical system, distortions in both the directions may increase or decrease, or a distortion in one of the directions may increase and a distortion in the other direction may decrease.

A specific example of the method of specifying the movement amount will be described. The movement amount of the optical system is compared with the change of the cross-sectional shape before and after the movement. Specifically, for example, the change in the ratio of the length of the two facing sides or the change in the length of each of the sides, etc., is compared. According to the results of this comparison, the amount of change (unit amount of change) in the cross-sectional shape when the optical system is moved only by a specified unit distance can be obtained. This process is executed, for example, by dividing the amount of change in the cross-sectional shape by the moving distance of the optical system. At this moment, a coefficient according to the corneal curvature, etc., may be considered. The movement amount is also obtained individually for the anteroposterior direction and the horizontal direction, respectively.

The controller 60 controls the drive unit 5 based on the displacement acquired as the above so as to move the optical system. The movement direction and the movement amount at this moment are a direction and a distance that correspond to such displacement.

In the above example, the cross-sectional shapes of the observation light regarding the two positions of the optical system are compared, but the accuracy of the position adjustment can be enhanced by acquiring and comparing cross-sectional shapes regarding three or more positions.

According to this modification, an accurate position adjustment of the optical system can be performed according to the individual eyes E.

By moving the optical system in directions including components of both the directions of the anteroposterior direction and the horizontal direction, it is possible to obtain displacements in both the directions during movement once. It is also possible to obtain a displacement in the anteroposterior direction by moving the optical system in the anteroposterior direction and, independently therefrom, obtain a displacement in the horizontal direction by moving the optical system in the horizontal direction.

Another modification of the method of computing the displacement of the optical system will now described. Firstly, a cross-sectional shape of the observation light is obtained as in the second embodiment (Steps 21-23, Step 26).

Next, the horizontal-displacement computing part 69 specifies the barycentric position of this cross-sectional shape. This process is executed by, for example, any known technique to obtain a barycentric position of a 2-dimensional image.

In addition, the horizontal-displacement computing part 69 obtains a distance from the barycentric position of each side of this cross-sectional shape. This process is executed by, on each side, obtaining a line that is orthogonal to the side and passes through the barycentric position, obtaining a line segment with the side and the barycentric position as both ends, and obtaining the length of this line segment.

Subsequently, regarding two pairs of two facing sides, the horizontal-displacement computing part 69 obtains a movement direction and a movement amount of the optical system such that the distances from the barycentric position to the two sides of each of the pairs become equal.

Here, the cross-sectional shape of the observation light has four sides as described above (refer to FIG. 9). The four sides are divided into two pairs of two facing sides. For example, in FIG. 9, they are divided into a pair composed of an upper side and a lower side and a pair composed of a left side and a right side.

The horizontal-displacement computing part 69 obtains a movement direction and movement amount of the optical system such that the distances from the barycentric position to the two sides of each of the pairs become equal. That is, it obtains a movement direction and movement amount of the optical system such that the cross-sectional shape of the observation light becomes a rectangular shape (a reference cross-sectional shape: refer to FIG. 11).

In a method of computing the movement direction and movement amount, for example, regarding each of the anteroposterior direction and the horizontal direction, information that correlates the difference between distances from the barycentric position to the two sides with the movement direction and movement amount of the optical system is previously stored, and by referring to this information, the movement direction and the movement amount can be obtained from the actual distance difference. Moreover, as in the above modification, it is possible to obtain the movement direction and the movement amount based on the change of the above distance difference in a plurality of positions.

〔Other Modification〕

A configuration to obtain both the movement direction and the movement amount of the head lens 13 or the optical system is described in the above embodiments and the modification, but it is also possible to configure to obtain only one of them. The method of obtaining it is as described in the above embodiments and the modification.

In the case of obtaining only a movement direction, it is possible to present information that shows the movement direction (upward or downward) of the head lens 13 or information that shows the movement direction (anterior or posterior, rightward or leftward) of the optical system. These information can be presented by using a display device (LCD, CRT, etc.), which is not shown, or can be presented via the eyepiece 37 by displaying it on a small LCD, etc., within the optical system. Moreover, it may also be presented as voice information.

Moreover, for example, the operator may start movement in the movement direction in response to an operation of the foot switch 8 and stop the movement at a desired position.

In the case of obtaining only the movement amount, it is possible to present information that shows the movement amount.

What is claimed is:

1. A surgical microscope apparatus comprising:
    an optical system including an illumination optical system configured to project illumination light onto an eye via an objective lens, an observation optical system configured to guide reflected light of the illumination light from the eye to an eyepiece via the objective lens, and a head lens positioned between the objective lens and the eye;

a driver configured to move the optical system;
a detector configured to detect the reflected light guided by the observation optical system; and
a controller configured to control the driver to change a relative position of the optical system with respect to the eye so that a cross-sectional pattern of the reflected light detected by the detector becomes a specified reference pattern.

2. The surgical microscope apparatus according to claim 1, wherein:
the illumination optical system projects light having a cross-section with a specified shape as the illumination light; and
the controller includes an analyzer configured to obtain a cross-sectional pattern of the reflected light based on a result of detection of the reflected light by the detector.

3. The surgical microscope apparatus according to claim 2, wherein:
the analyzer obtains luminance distribution in a cross-section of the reflected light as the cross-sectional pattern.

4. The surgical microscope apparatus according to claim 3, wherein:
the specified reference pattern is a reference distribution profile of luminance corresponding to the specified shape of the illumination light;
the driver includes a first drive mechanism configured to move the head lens in a direction of an optical axis of the objective lens; and
the controller controls the first drive mechanism so that a profile of luminance distribution of the reflected light becomes the reference distribution profile.

5. The surgical microscope apparatus according to claim 4, wherein:
the controller includes a storage configured to previously store an allowable range of luminance distribution based on the reference distribution profile and a determining part configured to determine whether the luminance distribution of the reflected light is within the allowable range, and controls the first drive mechanism so that it is determined that the luminance distribution is within the allowable range.

6. The surgical microscope apparatus according to claim 4, wherein:
the specified shape of a cross-section of the illumination light is rectangular; and
the reference distribution profile is a rectangular pulse shape.

7. The surgical microscope apparatus according to claim 5, wherein:
the specified shape of the cross-section of the illumination light is rectangular; and
the reference distribution profile is a rectangular pulse shape.

8. The surgical microscope apparatus according to claim 3, wherein:
the driver includes a first drive mechanism configured to move the head lens in a direction of an optical axis of the objective lens; and
the controller includes a computing part configured to obtain a movement direction and/or movement amount of the head lens based on the luminance distribution of the reflected light, and controls the first drive mechanism based on the movement direction and/or the movement amount.

9. The surgical microscope apparatus according to claim 8, wherein:
the controller controls the first drive mechanism to move the head lens after the luminance distribution of the reflected light is acquired by the analyzer;
the detector detects the reflected light of the illumination light after movement of the head lens;
the analyzer obtains new luminance distribution based on the result of detection of the reflected light; and
the computing part compares the luminance distribution before the movement with the new luminance distribution, and obtains the movement direction and/or movement amount of the head lens.

10. The surgical microscope apparatus according to claim 2, wherein:
the analyzer obtains a cross-sectional shape of the reflected light as the cross-sectional pattern.

11. The surgical microscope apparatus according to claim 10, wherein:
the specified reference pattern is a reference cross-sectional shape corresponding to the specified shape of the illumination light;
the driver includes a second drive mechanism configured to move the optical system in a direction orthogonal to an optical axis of the objective lens; and
the controller controls the second drive mechanism so that the cross-sectional shape of the reflected light becomes the reference cross-sectional shape.

12. The surgical microscope apparatus according to claim 11, wherein:
the controller includes a storage configured to previously store an allowable range of the cross-sectional shape based on the reference cross-sectional shape and a determining part configured to determine whether the cross-sectional shape of the reflected light is within the allowable range, and controls the second drive mechanism so that it is determined that the cross-sectional shape is within the allowable range.

13. The surgical microscope apparatus according to claim 11, wherein:
the specified shape of the cross-section of the illumination light is rectangular; and
the reference cross-sectional shape is rectangular.

14. The surgical microscope apparatus according to claim 12, wherein:
the specified shape of the cross-section of the illumination light is rectangular; and
the reference cross-sectional shape is rectangular.

15. The surgical microscope apparatus according to claim 11, wherein:
the driver includes a second drive mechanism configured to move the optical system in a direction orthogonal to an optical axis of the objective lens; and
the controller includes a computing part configured to obtain a movement direction and/or movement amount of the optical system based on the cross-sectional shape of the reflected light and the reference cross-sectional shape, and controls the second drive mechanism based on the movement direction and/or the movement amount.

16. The surgical microscope apparatus according to claim 15, wherein:
the specified shape of the cross-section of the illumination light is rectangular;
the reference cross-sectional shape is rectangular; and
the computing part obtains a barycentric position of the cross-sectional shape of the reflected light, obtains a distance from the barycentric position to each of four sides of the cross-sectional shape and, for two pairs of two facing sides in the cross-sectional shape of the reflected light, obtains the movement direction and/or movement amount of the optical system such that the distances to the two sides of each of the pairs are equal.

17. The surgical microscope apparatus according to claim 15, wherein:

the controller controls the second drive mechanism to move the optical system after the cross-sectional shape of the reflected light is acquired by the analyzer;

the detector detects the reflected light of the illumination light after movement of the optical system;

the analyzer obtains a new cross-sectional shape based on a result of detection of the reflected light; and the computing part compares the cross-sectional shape before the movement with the new cross-sectional shape, and obtains the movement direction and/or movement amount of the optical system.

* * * * *